(12) United States Patent
Razon

(10) Patent No.: US 10,376,734 B1
(45) Date of Patent: Aug. 13, 2019

(54) GAIT TRAINING EXERCISE AND ANALYSIS SYSTEMS FOR BODY SUPPORT SYSTEMS WITH ADJUSTABLE USER BODY WEIGHT FORCE

(71) Applicant: Eli Razon, Maple Glen, PA (US)

(72) Inventor: Eli Razon, Maple Glen, PA (US)

( * ) Notice: Subject to any disclaimer, the term of this patent is extended or adjusted under 35 U.S.C. 154(b) by 187 days.

(21) Appl. No.: 15/356,619

(22) Filed: Nov. 20, 2016

Related U.S. Application Data

(63) Continuation-in-part of application No. 14/816,041, filed on Aug. 2, 2015, now Pat. No. 9,498,696.

(60) Provisional application No. 62/047,011, filed on Sep. 7, 2014, provisional application No. 62/292,799, filed on Feb. 8, 2016.

(51) Int. Cl.
| | |
|---|---|
| A61B 5/11 | (2006.01) |
| A63B 22/00 | (2006.01) |
| A63B 22/02 | (2006.01) |
| A63B 24/00 | (2006.01) |
| A63B 21/00 | (2006.01) |
| A63B 71/00 | (2006.01) |
| G06K 9/00 | (2006.01) |

(52) U.S. Cl.
CPC ......... *A63B 22/0046* (2013.01); *A61B 5/112* (2013.01); *A63B 21/00181* (2013.01); *A63B 22/025* (2015.10); *A63B 24/0006* (2013.01); *A63B 24/0062* (2013.01); *A63B 24/0087* (2013.01); *A63B 71/0009* (2013.01); *G06K 9/00348* (2013.01); *A63B 2071/0018* (2013.01); *A63B 2220/56* (2013.01); *A63B 2220/806* (2013.01)

(58) Field of Classification Search
CPC ............ A63B 22/0046; A63B 2/00181; A63B 24/0062; A63B 71/0009; A63B 24/0006; A63B 24/0087; A63B 22/025; A63B 2220/56; A63B 2220/806; A63B 2071/0018; G06K 9/00348; A61B 5/112
See application file for complete search history.

(56) References Cited

U.S. PATENT DOCUMENTS

| | | | | |
|---|---|---|---|---|
| 4,813,436 A | * | 3/1989 | Au ........................ | A61B 5/1038 356/620 |
| 6,430,997 B1 | * | 8/2002 | French ............... | A63B 24/0003 73/379.04 |
| 7,125,388 B1 | * | 10/2006 | Reinkensmeyer ........................... | A63B 69/0064 601/5 |
| 8,012,107 B2 | * | 9/2011 | Einav ...................... | G06F 19/00 601/5 |
| 8,088,045 B2 | * | 1/2012 | Hoffman .............. | A63B 21/055 482/1 |
| 8,246,354 B2 | * | 8/2012 | Chu ................... | A63B 22/0292 434/258 |

(Continued)

*Primary Examiner* — Andrew S Lo

(57) ABSTRACT

Gait analysis systems are provided with body support systems for user's self-adjustment of body weight force when ambulating with the body support systems. The gait analysis systems with the body support systems can be used with a treadmill or over a fixed surface for gait training and analysis with the ability to adjust the user's body weight force during the collection of gait data. Gait data for analysis is collected by an array of sensors mounted on the body support systems in various combinations for sensing gait movement, video imaging, heel strike and toe off states, video processing, feet pressure maps and electromyography.

21 Claims, 31 Drawing Sheets

(56) References Cited

U.S. PATENT DOCUMENTS

| | | | | |
|---|---|---|---|---|
| 8,622,747 B2* | 1/2014 | Chu | ................... | A63B 22/0292 |
| | | | | 434/258 |
| 9,498,401 B2* | 11/2016 | Herr | .................... | A61H 1/0255 |
| 9,782,659 B2* | 10/2017 | Yamazaki | ........... | A63B 71/0054 |
| 2007/0275830 A1* | 11/2007 | Lee | ...................... | A61B 5/1038 |
| | | | | 482/54 |
| 2008/0004550 A1* | 1/2008 | Einav | ...................... | G06F 19/00 |
| | | | | 601/33 |
| 2010/0152629 A1* | 6/2010 | Haas, Jr. | .............. | A61B 5/1038 |
| | | | | 601/34 |
| 2010/0298102 A1* | 11/2010 | Bosecker | ............... | A61H 1/005 |
| | | | | 482/54 |
| 2011/0294624 A1* | 12/2011 | Burnfield | ............ | A61H 1/0214 |
| | | | | 482/7 |
| 2016/0007885 A1* | 1/2016 | Basta | ................... | A61B 5/1038 |
| | | | | 482/5 |
| 2016/0144238 A1* | 5/2016 | Brunner | ............. | A63B 22/0235 |
| | | | | 482/9 |
| 2016/0166879 A1* | 6/2016 | Dilli | ................... | A63B 24/0062 |
| | | | | 482/8 |
| 2017/0087416 A1* | 3/2017 | Hu | .......................... | A61B 5/015 |
| 2018/0043208 A1* | 2/2018 | Foster | ............... | A63B 22/0235 |

\* cited by examiner

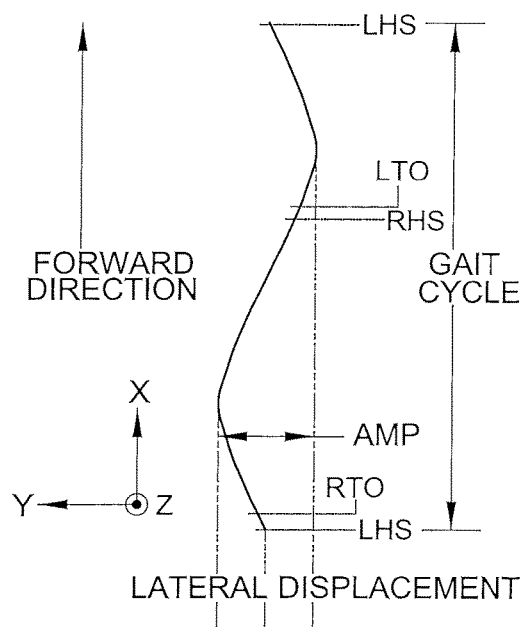
FIG. 1
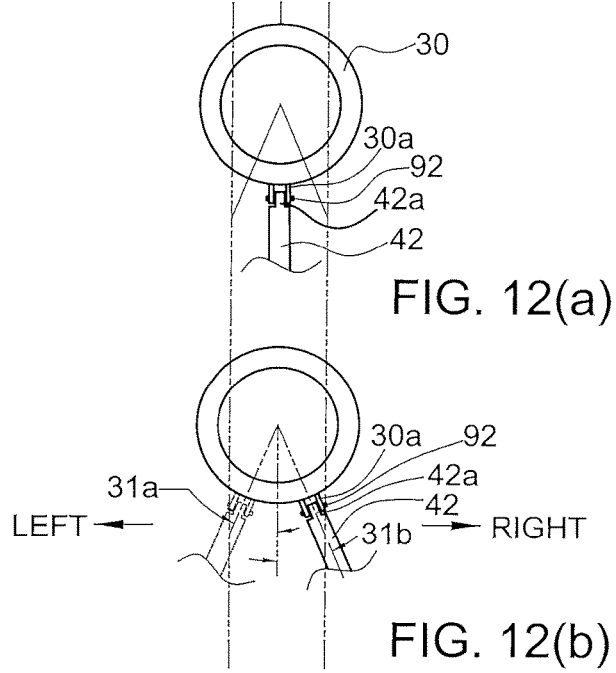
FIG. 12(a)
FIG. 12(b)
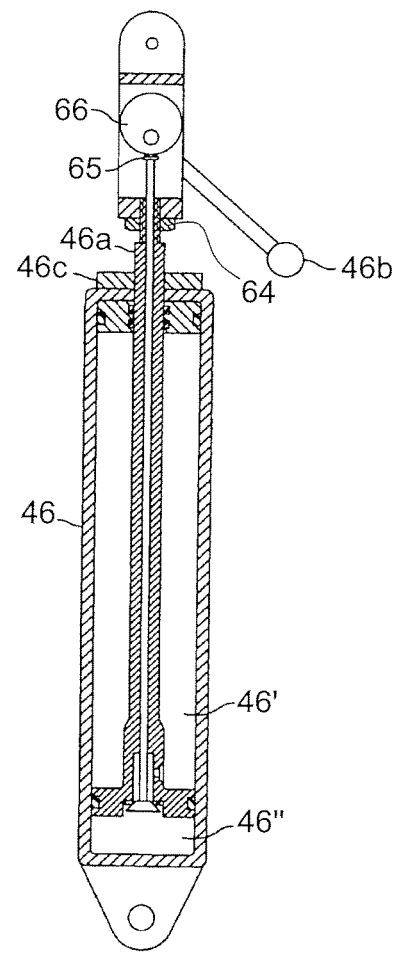
FIG. 11

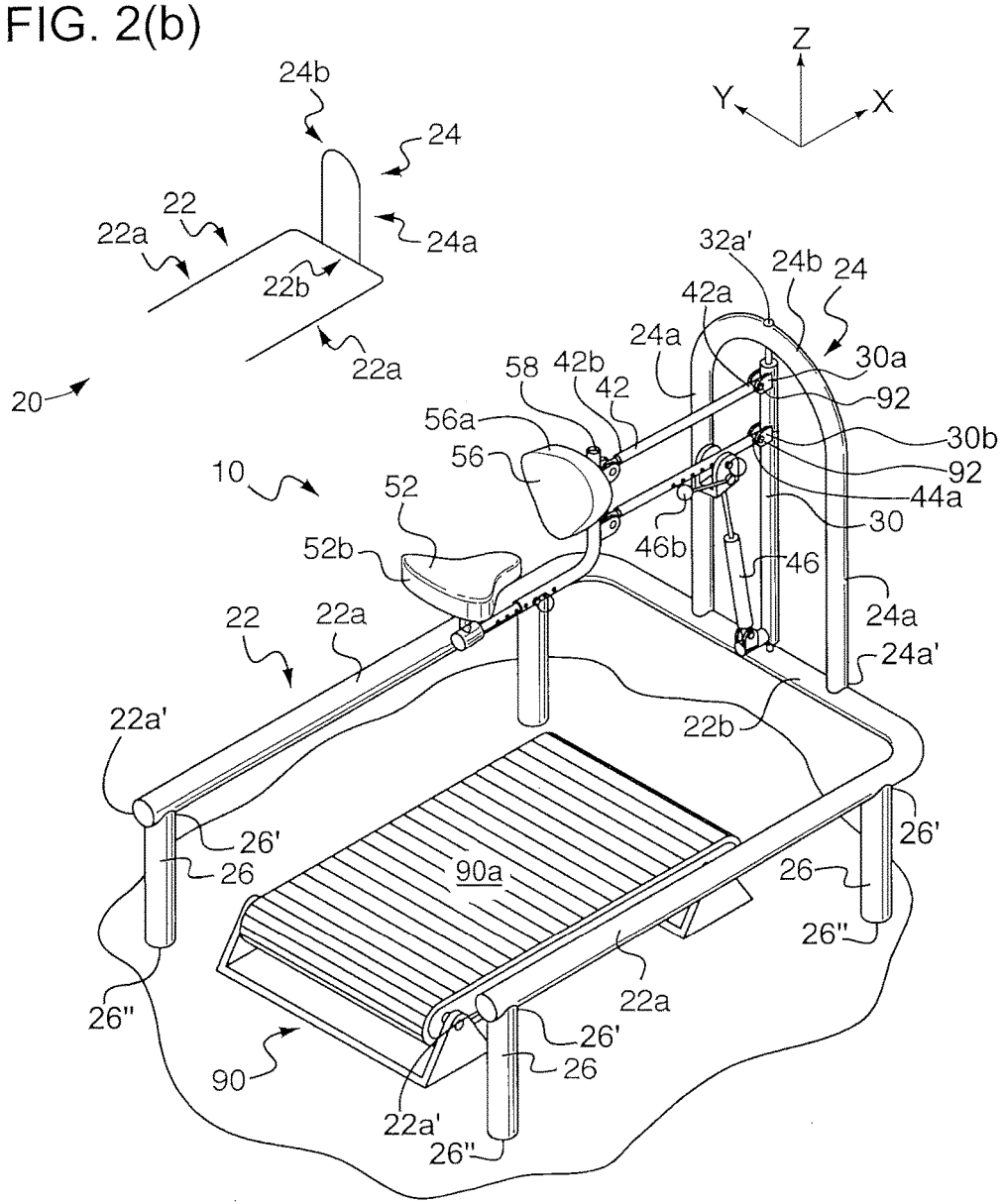

ES = encoder (COM) sensors  
VI = video imaging sensors  
FPS = feet pressure sensora  
T/H-SS = toe/heel switch sensors  
EMG = electromyographic sensors

X = INCLUDED  
X (OP) = OPTIONAL SENSORS  
X (IP) = VIDEO IMAGING AND PROCESSING

| GAIT SENSORS | SAMPLE ALTERNATIVE ANALYSIS SYSTEMS | | | | |
|---|---|---|---|---|---|
| | 1 | 2 | 3 | 4 | 5 |
| ES | X | X | X | X | X |
| VI | X | X | X (IP) | X (IP) | X (IP) |
| FPS | | | | X | X |
| T/H-SS | | X | X | X (OP) | X (OP) |
| EMG | | | | | X |

GAIT TRAINING EXERCISE AND ANALYSIS SYSTEMS FOR BODY SUPPORT SYSTEMS WITH ADJUSTABLE USER BODY WEIGHT FORCE

CROSS REFERENCE TO RELATED APPLICATIONS

This application is a continuation-in-part of U.S. patent application Ser. No. 14/816,041 filed Aug. 2, 2015, which application claims the benefit of U.S. Patent Application No. 62/047,011 filed Sep. 7, 2014, the disclosures of which applications are incorporated herein by reference.

This application claims the benefit of U.S. Patent Application No. 62/292,799 filed Feb. 8, 2016, the disclosure of which application is incorporated herein by reference.

FIELD OF THE INVENTION

The present invention generally relates to a gait analysis system used with body support systems for gait training exercise and analysis over a fixed surface or on a treadmill, and in particular to such systems where the body support system includes provisions for the ability to adjust the user's body weight force while over a fixed surface or on the treadmill surface.

BACKGROUND OF THE INVENTION

A treadmill is a device that can be used for exercising a human's pelvis, hips, knees and ankles by walking (more generally described as ambulating) or running while basically remaining in a relatively fixed position over the treadmill's moving surface. Treadmill exercise can also be of aerobic benefit. Physically impaired or disabled individuals that are confined to a wheelchair or similar mobility aids, but can still safely exercise their pelvis, hips, knees and/or ankles have difficulty getting on and off of the treadmill surface for exercise. They may also experience difficulty in balancing themselves while exercising on the treadmill surface and may require a reduction in body weight forces on the treadmill surface while exercising on the treadmill surface.

During ambulation, the human body's center of mass (COM) is propelled forward. However the body's center of mass (or gravity) also moves vertically and laterally. The total lateral displacement of the center of mass is generally described in the art as tracing a sinusoidal curve with amplitude (AMP in FIG. 1) that can range from around one inch to 5 inches. The greatest lateral excursion of the center of mass occurs at the end of midstance when the body is supported by one leg and begins to move from force absorption at impact to force propulsion forward. Thus, only one full lateral oscillation of the center of gravity (to the right and left) occurs during a gait cycle as illustrated in FIG. 1 which is a view looking down on a treadmill surface with the "FORWARD DIRECTION" arrow facing the front of a typical treadmill where a treadmill console, if used, would be located. Further the degree of lateral displacement (AMP) decreases in going from slow to fast ambulation (for example from 5 inches at 0.1 mile per hour to one inch at 1 mile per hour) and conversely, decreases in going from fast to slow ambulation.

U.S. Pat. No. 5,569,129 discloses a user gait training apparatus that can be used with a treadmill. The apparatus comprises unitary device 21 that can be rolled along the floor to which a harness means 33 can be user connected whereby a user in the harness can be vertically raised or lowered to alter body weight force. The user must put on the harness and body weight force adjustment is accomplished by overhead connection to device 21. The device may be positioned over a treadmill surface so that the user can ambulate on the treadmill surface after having entered the harness. The device allows for forward body center of mass movement. Vertical center of mass movement is restricted by the overhead harness connection to the device and there is no provision for lateral body center of mass movement. Thus gait exercising on a treadmill with the device does not allow for freedom of body (center of mass) movement in all three directions (forward, vertical and lateral) as in a normal human gait during ambulation.

U.S. Pat. No. 8,151,812 B2 discloses a wheeled walker with a seat assembly that a user can dynamically raise or lower in the vertical direction so that the user can adjust the seat assembly's vertical height to mount the wheeled walker and then dynamically raise or lower the seat assembly to adjust the degree of body force weight on the walking surface. Thus the wheeled walker allows for forward body center of mass movement and an adjustable body vertical center of mass movement. At best restricted lateral body center of mass movement can be provided to a limited degree by the caster wheels.

U.S. Pat. No. 6,821,233 B1 has a special harness connected to the user that makes it hard to get in and out of and also the lifting is done overhead. The ability to dynamically stand or to experience normal gait is very limited in the vertical motion, and with no weight-shifting lateral (left and right) movement which are critical at low walking speeds. The harness is very difficult to get in and out of for users that are wheelchair bound and has no access to reach the lower extremities to assist in physical rehabilitation.

U.S. Pat. No. 8,464,716 B2 discloses a differential air pressure system that comprises a user's chamber for maintaining an air pressure differential upon the user's body while exercising on a treadmill surface.

It is one object of the present invention to provide a gait analysis system for a treadmill body support system for gait training exercise on a treadmill where the body support system has means for adjusting the user's body weight force.

It is another object of the present invention to provide a gait analysis system for a body support system for gait training exercise over a fixed surface where the body support system has means for adjusting the user's body weight force.

BRIEF SUMMARY OF THE INVENTION

In one aspect the present invention is a gait analysis system in combination with a body support system where a user of the body support system can self-adjust the user's body weight force during ambulation in the body support system over a treadmill or fixed surface during collection of data for the gait analysis. In one embodiment of the invention, forward and vertical gait movements of the user are measured with distance sensors on the body support system and observed with video sensors connected to the body support system. In other embodiments of the invention lateral gait movements are also measured with distance sensors on the body support system. In other embodiments of the invention toe and heel bi-state sensors are attached to the user to sense each foot's heel-strike-to-heel-off and toe-off-to-toe-touch time periods in each gait cycle and the heel and toe time periods are coordinated with the measured gait movements and video display. In other embodiments of the invention the video images provided by the video data from the video sensors are image processed for user body parameters related to gait movements and coordinated with the measured gait movements, video display and/or processing, and the measured heel and toe time periods. In other embodiments of the invention pressure sensing of the user's feet on the treadmill or fixed floor are measured either with a non-wearable or wearable foot pressure sensors for coordination with the other sensed gait data.

In another aspect the present invention is a method of gait analysis with a body support system where a user of the body support system can self-adjust the user's body weight force during ambulation in the body support system over a treadmill or fixed surface during collection of data for the gait analysis. In one embodiment forward and vertical gait movements are used to analyze the position of the user's center of mass during ambulation with forward and vertical gait measurement sensors attached to the body support system and movement of the user's lower body is observed with video sensors connected to the body support system. In other embodiments of the invention lateral gait movements are also used. In other embodiments of the invention each foot's heel-strike-to-heel-off and toe-off-to-toe-touch time periods in each gait cycle are analyzed by toe and heel bi-state sensors attached to the user and the time periods are correlated with movement of the user's center of mass and video display of the user ambulating in the body support system. In other embodiments of the invention the video images provided by the video data are image processed for user body parameters related to movement of the user's center of mass and correlated with movement of the user's center of mass, the video display of the user ambulating in the body support system and the measured heel and toe time periods. In other embodiments of the invention pressure patterns of the user's feet on the treadmill or fixed floor while ambulating in the body support system are measured either with a non-wearable or wearable foot pressure sensors for coordination with the other sensed gait data.

The above and other aspects of the invention are further disclosed in this specification and the appended claims.

BRIEF DESCRIPTION OF THE DRAWINGS

The figures, in conjunction with the specification and claims, illustrate one or more non-limiting modes of practicing the invention. The invention is not limited to the illustrated layout and content of the drawings.

FIG. 1 diagrammatically illustrates typical lateral body center of mass displacement through a gait cycle and relative positioning of each heel strike which begins the moment when the heel of each body support system user's foot touches a treadmill or fixed surface and relative positioning of each toe off which begins the moment when the user's toe leaves a treadmill or fixed surface.

FIG. 2(a) is an isometric view of one example of a treadmill body support system for gait training exercise on a treadmill with the body support system installed over a treadmill surface.

FIG. 2(b) diagrammatically illustrates references to the arms and foot of "U" shaped frame base and frame bridge shown in FIG. 2(a).

FIG. 11 is a vertical section view of the body support spring means shown in FIG. 6 at a right angle to section 8B-8B shown in FIG. 6 in its preferred embodiment of a pressurized gas cylinder in its closed or locked (static mode) position which limits the movement of the pressurized gas within the upper interior chamber 46' and lower interior chamber 46" of the gas cylinder.

FIG. 12(a) and FIG. 12(b) illustrate diagrammatically relative to FIG. 1 how rotation of lateral displacement rotational means 30 permits freedom of lateral displacement of the user's center of mass while ambulating on the treadmill surface in a treadmill body support system used in a gait analysis system of the present invention.

FIG. 15(*b*) is a detail view of one example of a forward (X) direction gait measurement sensor used with the gait analysis system shown in FIG. 13 or FIG. 14.

FIG. 15(*c*) is a detail view of one example of a vertical (Z) direction distance sensor used to measure Z distance over a time period for the gait analysis system shown in FIG. 13 or FIG. 14.

FIG. 18(*b*) is a detail example of one example of a forward (X) direction gate measurement distance sensor used to measure X distance over a time period for the gait analysis system shown in FIG. 16 or FIG. 17.

FIG. 18(*c*) is a detail example of one example of a lateral (Y) direction gate measurement distance sensor used to measure Y distance over a time period for the gait analysis system shown in FIG. 16 or FIG. 17.

FIG. 21(*b*) illustrates combinations of sensors used in preferred, but not limiting, examples of the gait training exercise and analysis systems for body support systems with adjustable user body weight support of the present invention.

DETAILED DESCRIPTION OF THE INVENTION

Figure 5:
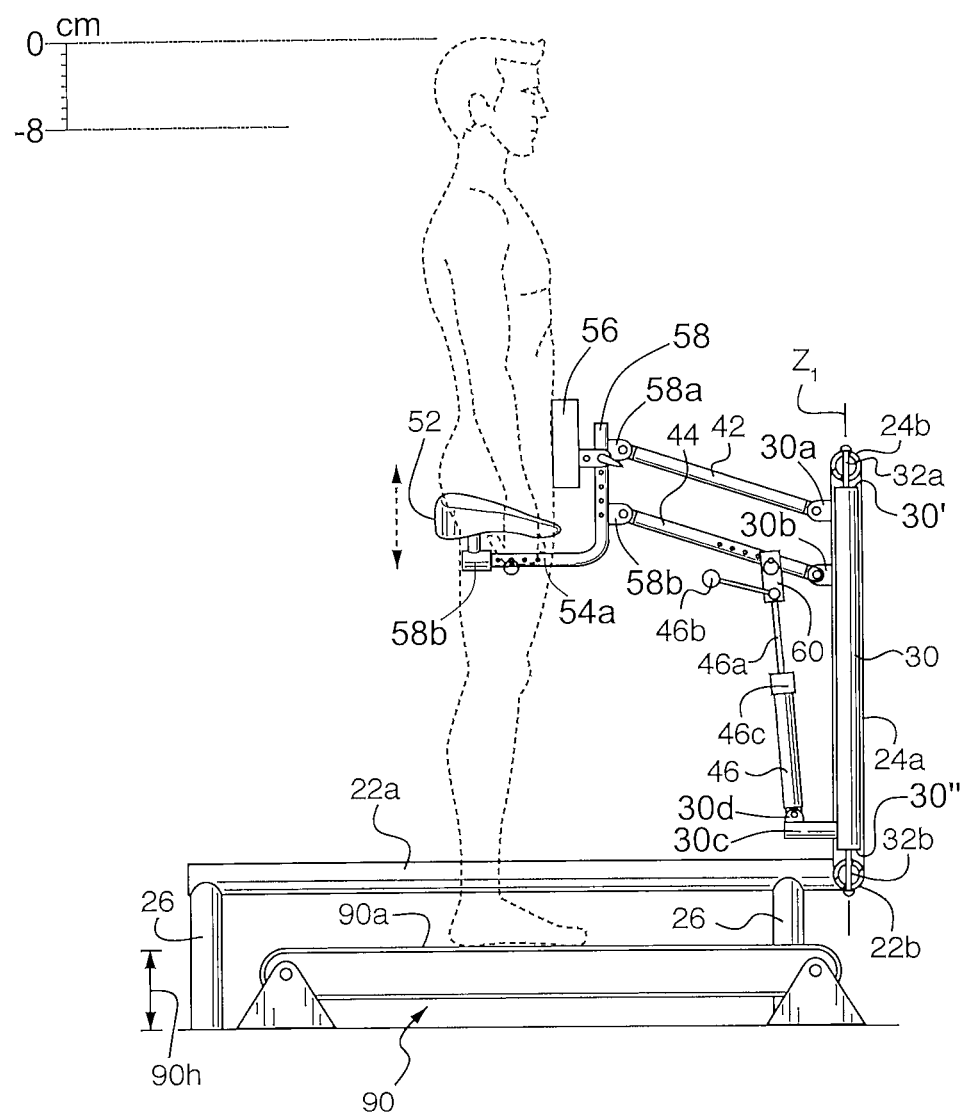
FIG. 5 is a right side elevation view of the treadmill body support system shown in FIG. 2(a) with the seating assembly shown in a raised vertical position (treadmill body support standing position) for stabilized fully erect standing of the illustrated user on the treadmill surface and a partial cross sectional view of bridge foot 24b and base foot 22b to expose lateral displacement rotational means 30.

One embodiment of a treadmill body support system 10 for gait training exercise on a treadmill for use with a gait analysis system of the present invention is shown in FIG. 2(*a*) through FIG. 5 as positioned over treadmill 90 which is partially shown diagrammatically and represents either a consumer or commercial treadmill, for example, that may, but not necessarily, have a front console with a display and control unit and/or handrails for a user to optionally hold with his or hers hands while in the treadmill body support system over the treadmill. More broadly, the treadmill body support system can be positioned over any device for ambulating or running on without actual forward movement. The treadmill is not necessarily a component of treadmill body support system 10; that is, the treadmill body support system can be arranged for placement over an existing treadmill, for example, with a console located forward of a treadmill body support system; that is, to the right and forward (in the X-direction) of the frame bridge 24 of the body support system as shown in FIG. 2(*a*) so that the user may optionally have control of the treadmill's operating parameters such as speed and inclination of the treadmill surface.

Figure 3:
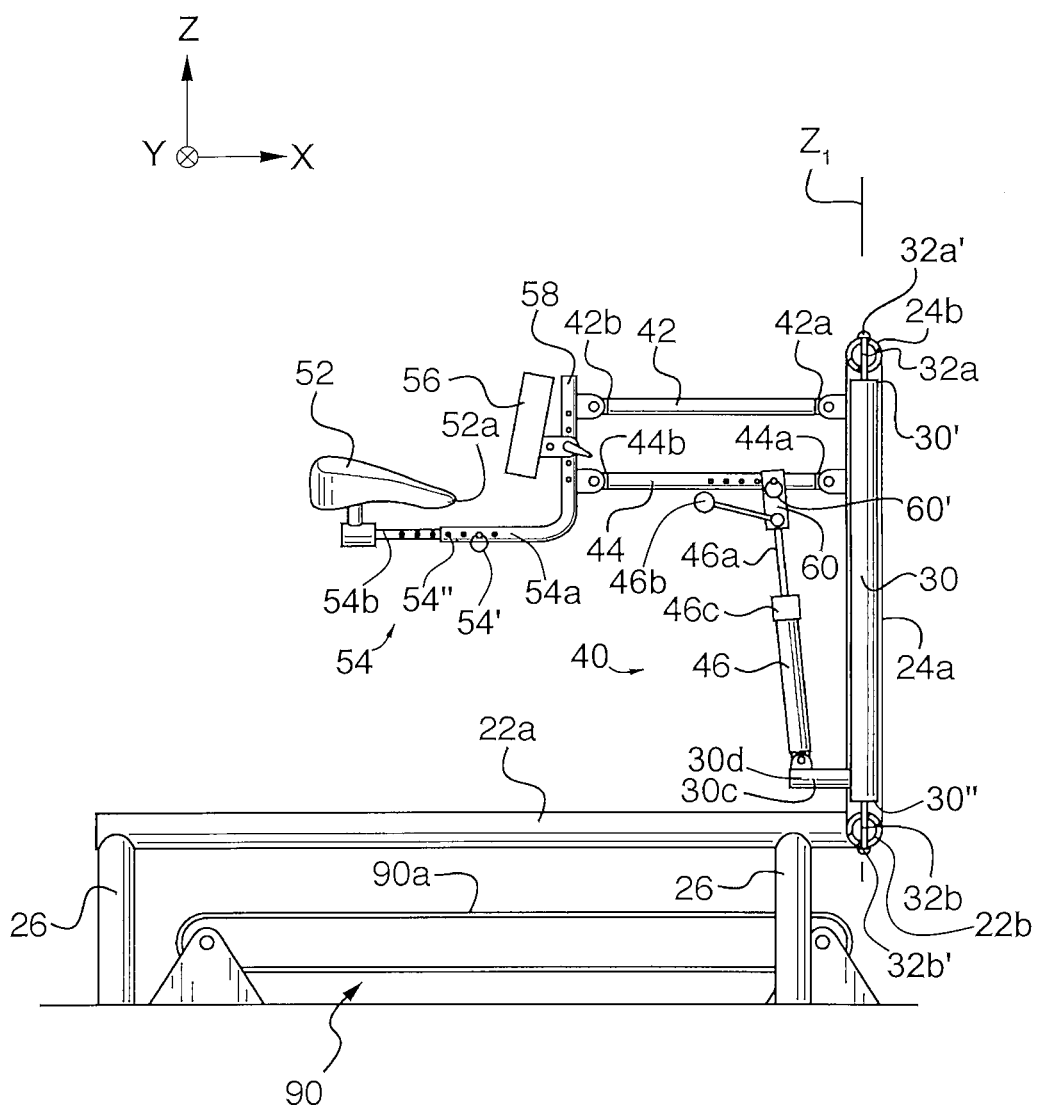
FIG. 3 is a right side elevation view of the treadmill body support system shown in FIG. 2(a) with the seating assembly shown parallel to the horizontal reference plane and a partial cross sectional view of bridge foot 24b and base foot 22b to expose lateral displacement rotational means 30.
Figure 4:
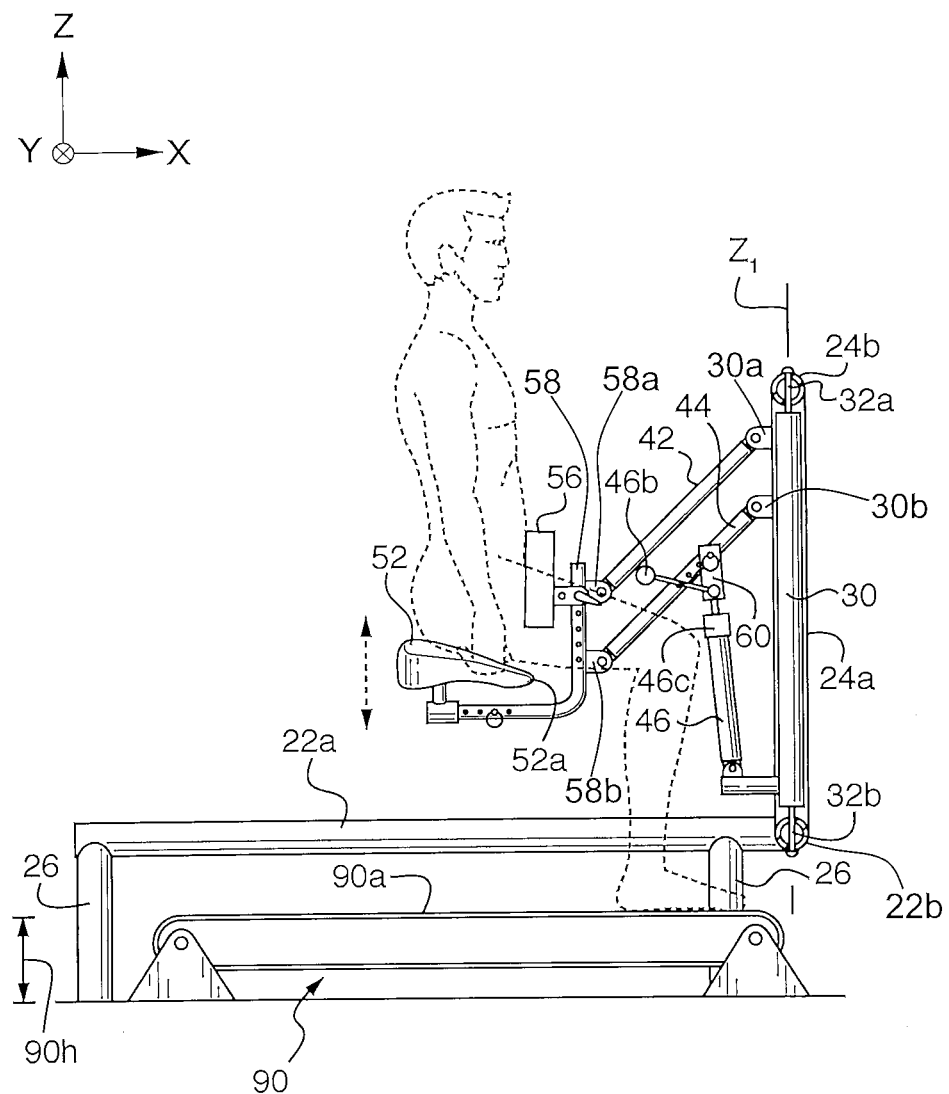
FIG. 4 is a right side elevation view of the treadmill body support system shown in FIG. 2(a) with the seating assembly shown in a lowered vertical position (treadmill body support sitting height position) for user transfer to and from the treadmill support system, for example, from, or to, a wheelchair positioned behind the seated illustrated user (in dotted lines) shown in the figure, and a partial cross sectional view of bridge foot 24b and base foot 22b to expose lateral displacement rotational means 30.

In the embodiment of treadmill body support system 10 shown in the figures apparatus frame assembly 20, which may be referred to as the main frame, comprises frame base 22, frame bridge 24, and a plurality of frame elevation lifting means which in this example are frame legs 26. In this embodiment frame base 22 and frame bridge 24 each comprise a "U" shaped structure that can be a tubular material formed on rolling forming and bending apparatus into the illustrated "U" shapes. In other examples the main frame may be otherwise formed as long as it provides for positioning of the treadmill body support system over a treadmill surface and mounting of the lateral displacement rotational means with support for the support lever, position stabilizing arm and adjustable body weight support spring means. Reference to the arms and foot of each "U" shaped structure is diagrammatically illustrated in FIG. 2(*b*). In this example frame legs 26 comprise four tubular legs that are cylindrical in shape. Each of the legs has an upper leg end 26' suitability distributed and attached to frame base 22. In this example a frame leg is suitably fixed at upper leg end 26' to the opposing base arm ends 22*a*' and 22*a*" of each of two base arms 22*a* of "U" shaped frame base 22. The function of the legs in this example is to raise frame base 22 above the vertical height 90$_h$ (from a horizontal reference plane as shown, for example, in FIG. 4) of the moving platform of the treadmill that is typically a wide conveyor belt driven by an electric motor or flywheel; the moving platform will be referred to as treadmill surface 90*a* upon which a user's feet make contact with when the user is in the treadmill body support system whether or not the treadmill surface is moving. The horizontal reference plane may be, for example, the floor or platform that the treadmill stands on. The lower leg end 26" of each leg, which is opposite the upper end 26' rests on a horizontal surface below the treadmill surface in this example. In other examples each leg may consist of two or more telescoping sections to provide adjustability of the height of the frame base above the treadmill surface. Generally the longitudinal lengths of each one of the plurality of legs are equal so that frame base 22 lies in a plane parallel to the horizontal reference plane and the treadmill surface. In some applications it may be advantageous to have unequal leg lengths, for example, to establish a sloped frame base planar orientation relative to the horizontal reference plane. In some embodiments wheels may be provided at the lower leg ends to move the treadmill body support system to and from over a treadmill surface as illustrated for example in FIG. 13 or FIG. 14.

The lower bridge arm ends 24a' of the "U" shaped frame bridge's bridge arms 24a are suitably attached to the base foot 22b of "U" shaped frame base 22. The frame bridge is generally centered vertically (Z-direction) over base foot 22b of the "U" shaped frame base as shown in FIG. 2(a).

Rotational shaft 30 represents one example of a lateral displacement rotational means used in the treadmill body support system. Rotational shaft 30 is pivotally attached between the vertical center (along axis $Z_1$) of bridge foot 24b of "U" shaped frame bridge 24 and the vertical center (along axis $Z_1$) of base foot 22b of "U" shaped frame base 22, and provides gait freedom of motion in the Y-direction (that is, lateral displacement). One example of such pivotal attachment is shown in the figures. In this example rotational shaft 30 is a hollow cylindrical shaft that is pivotally attached to the vertical center of the bridge foot of "U" shaped frame bridge 24 by top pin 32a and the vertical center of the base foot of the "U" shaped frame base 22 by bottom pin 32b. Top pin 32a passes through vertically oriented top and bottom pin openings in bridge foot 24b of the frame bridge and is suitably connected to top shaft end of rotational shaft 30, for example, by top threaded hole (shrink-fit) fitting 30' disposed within the hollow interior of the top shaft end of rotational shaft 30, so that when top pin has a screw thread, the top pin can be screwed into the threaded hole fitting 30'. A similar arrangement is illustrated for bottom pin 32b. Bottom pin 32b passes through vertically oriented top and bottom pin openings in base foot 22b of the frame base and is suitably connected to bottom shaft end of rotational shaft 30, for example, by bottom threaded hole (shrink-fit) fitting 30" disposed within the hollow interior of the bottom shaft end of rotational shaft 30, so that when bottom pin has a screw thread, the bottom pin can be screwed into the threaded hole fitting 30". For this example of pivoting attachment, rotational shaft 30 is free to rotate about a Z-axis, $Z_1$, that is parallel to orthogonal X-Y planes since the top and bottom pins are free to rotate about the pin openings in the frame bridge and frame base, respectively, while being held within the frame bridge and frame base, respectively, by top pin head 32a' and bottom pin head 32b'.

FIG. 12(a) and FIG. 12(b) illustrate diagrammatically relative to FIG. 1 how rotation of lateral displacement rotational means 30 permits freedom of lateral displacement of the user's center of mass while ambulating on the treadmill surface in the treadmill body support system. In FIG. 12(a), looking down at a horizontal cross section of lateral displacement rotational means 30, position stabilizing arm 42 is shown in the neutral centered position. As a user in the treadmill body support system ambulates on the moving treadmill surface, the user can experience unrestrained lateral gait movement as lateral displacement rotational means 30 rotates between left lateral displacement angle 31a (from the neutral center position) and right lateral displacement angle 31b (from the neutral center position) as shown in FIG. 12(b) where position stabilizing arm 42 is shown in double image for individual left (in dotted lines) and right (in solid lines) lateral displacements.

In another embodiment the lateral displacement rotational means may be a hollow cylindrical shaft that is fitted over a fixed shaft extending from the vertical center of bridge foot 24b of the frame bridge to the vertical center of the base foot 22b of the base frame. One or more ball bearings can be positioned between the outer surface of the fixed shaft and inner surface of the hollow cylindrical shaft so that the hollow cylindrical shaft rotates freely about a Z-axis in a similar fashion as described for rotational shaft 30.

In other examples optional rotational stops can be provided to limit the left and right rotation limits of the lateral displacement rotational means to correct or limit an excessive lateral displacement of body center of mass.

One example of a vertical (Z direction) adjustment system of the treadmill body support system is vertical adjustment system 40 comprising position stabilizing arm 42, support lever 44 and body weight support means.

Position stabilizing arm 42 has stabilizing arm opposing ends 42a and 42b and support lever 44 has support lever opposing ends 44a and 44b. Position stabilizing arm end 42a and support lever end 44a are rotationally connected to rotational shaft 30, and position stabilizing arm end 42b and support lever end 44b are rotationally connected to front body support post 58. In this example rotational shaft connecting means are "U" shaped connectors 30a and 30b and front body support post connecting means are "U" shaped connectors 58a and 58b. Position stabilizing arm end 42a and support lever end 44a are fitted respectively within "U" shaped connectors 30a and 30b, and position stabilizing arm end 42b and support lever end 44b are fitted respectively within "U" shaped connectors 58a and 58b. A suitable fastener 92, such as a cotter pin or threaded screw (with bolt) passes through horizontally aligned holes in each combination of a "U" shaped connector and the respective position stabilizing arm end or support lever end within the "U" shaped connector to allow rotation of the position stabilizing arm and the support lever about a Y-axis. In other examples, other types of interconnecting means between the position stabilizing support arm and support lever, and the rotational shaft and front body support post, that allow rotation of the position stabilizing support arm and support lever about the Y-axis relative to the rotational (about a Z-axis) shaft and front body support post 58 (with freedom of motion in the vertical (or Z-axial direction) can be used.

Support lever 44 is attached to a body weight support spring means. The body weight support spring means lowers or raises the support lever 44. The position stabilizing arm 42 is likewise lowered or raised in tandem with the support lever 44 in response to the activation of the body weight support spring means. The body weight support spring means lowers or raises the body seating assembly simultaneously with the lowering or raising of support lever 44 and position stabilizing arm 42. One example of a body seating assembly is body seating assembly 50 comprising seat 52, seat support extension 54, front body support 56 and front body support post 58.

In the present example, support lever 44 is at an elevational (Z-directional) height below position stabilizing arm 42. In alternative embodiments, support lever 44 can be positioned above position stabilizing arm 42 so long as support lever 44 and position stabilizing arm 42 remain parallel to each other and the support lever 44 and position stabilizing arm 42 are of the same length.

As seat 52 is lowered toward, or raised away, from the treadmill surface 90a through the activation of the body weight support spring means, seat 52 and front body support 56 maintain a constant angle with respect to the treadmill surface. The rotational connections between rotational shaft 30 and front body support post 58 at the opposing ends of both position stabilizing arm 42 and support lever 44, along with their parallel orientation and equality of length enable seat 52 to rotate or swivel to the degree necessary to maintain seat 52 and front body support 56 at a constant angle with respect to treadmill surface 90a. The maintenance of this angle with respect to the treadmill surface imparts stability and balance to the user while positioned over the treadmill surface. The preservation of this angle facilitates pelvic stability and aids in enabling the stabilized user's fit imparted by the seat and front body support to be realized. The preservation of this angle with respect to the treadmill surface allows the user in the treadmill body support system to maintain the user's body orientation, posture and pressure points upon the seat and body support as the user switches back and forth between standing on the treadmill surface (either stationary or while ambulating or running), partially standing on the treadmill surface (transitioning between a standing and sitting position) and sitting position (for example, for transfer to, or from, a wheelchair on or over the treadmill surface) and thereby maintain balance.

Figure 7:
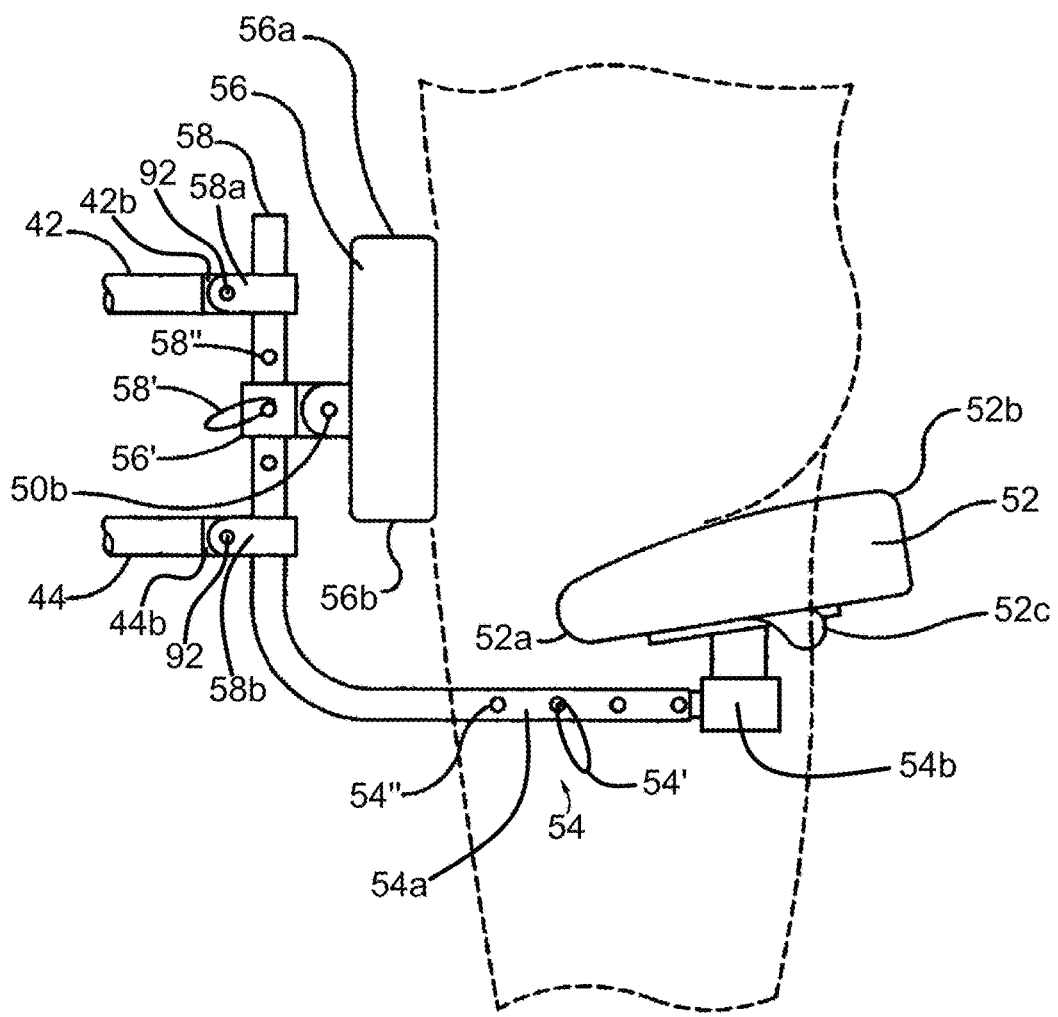
FIG. 7 is a left side elevation view of the seat, seat support extension, front body support and front body support post of the treadmill body support system shown in FIG. 2(a) with an illustrated user shown fitted in the system and in the treadmill body support standing position.
Figure 9:
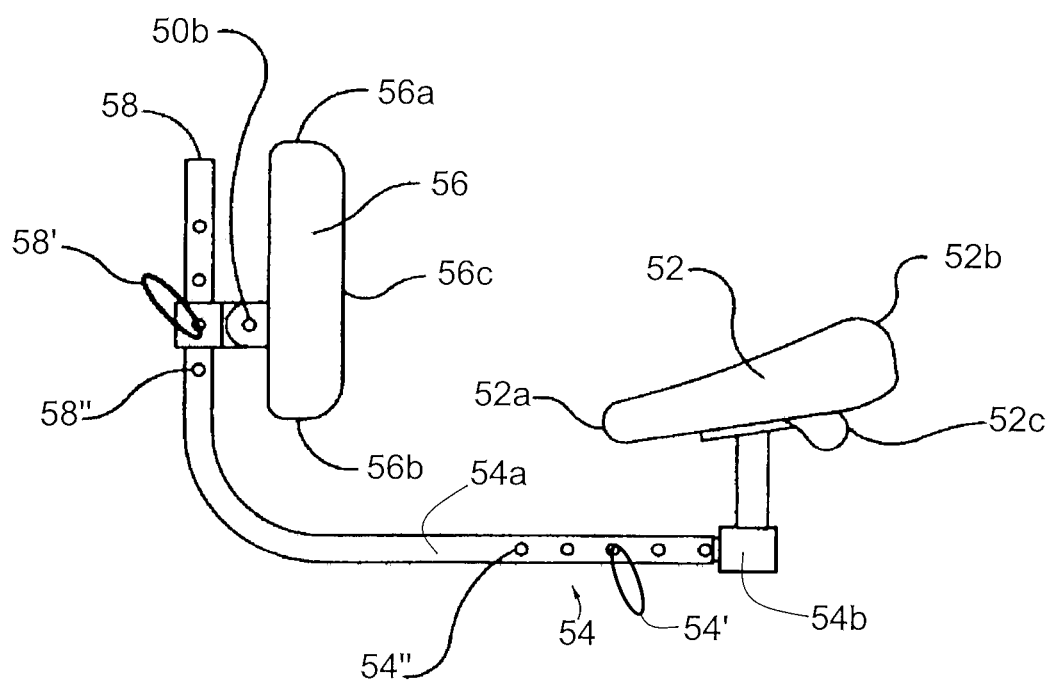
FIG. 9 is a left side elevation view of the seat assembly used with the treadmill body support system shown in FIG. 2(a).

Reference is made to FIG. 7 and FIG. 9 showing a side view of seat 52 in the example shown in the drawings. The seat preferably has a broad width in the back to support a user's posterior that tapers to a narrower width in the front of the seat. The seat is mounted on a seat support extension 54. Seat support extension 54 connects to the front body support post 58. In the embodiment shown in the drawings seat support extension 54 comprises non-telescoping seat support extension section 54a into which telescoping seat support extension section 54b can slide into or out of. Telescoping seat support extension section 54b has a fitting at one end that attaches the telescoping seat support extension section to seat 52.

In a preferred embodiment, the front body support post 58 and seat support extension 54 are separate sections of a continuous curved member in which a first section of seat support extension 54 and a second section of front body support post 58 are disposed at an angle close to 90 degrees or slightly in excess of or less than 90 degrees as illustrated, for example, in FIG. 7 and FIG. 9.

The seat can be adjustably positioned along the seat support extension 54 by sliding telescoping seat support extension section 54b, which is attached to the seat at one end, into or out of non-telescoping seat support extension section 54a to move the seat respectively toward or away from the front body support 56. The seat can be locked into position by means of an adjustment pin 54' with loop to facilitate the removal or insertion of the pin into any one of the several regularly spaced-apart openings 54" along the seat support extension 54. The seat front 52a can be tilted downward or upward with seat back 52b correspondingly tilted upward or downward by means of a seat tilt adjustment lever 52c which activates loosening means to allow the tilt of the seat to be adjusted or tightening means to lock the tilt of the seat into a fixed position. Alternatively an adjustment nut can activate the loosening or tightening means.

The front body support 56 is adjustably positioned upon the front body support post 58 by means of a front body support connector 56' which slides along the front body support post 58 in a substantially vertical up or down direction. The elevational height and position of the front body support can be locked by means of adjustment pin 58' with loop to facilitate the removal or insertion of the pin into any one of the regularly spaced-apart openings 58" along the front body support post 58. The front body support 56 is attached to the front body support post 58 by a swivel joint 50b allowing the front body support to tilt or swivel so that the front body support top edge 56a can move either toward or away from seat 52 as front body support bottom edge 56b correspondingly moves in the opposite direction either away from or toward the seat. The front body support will swivel as the user's body contacts the front surface 56c of the front body support and in response to the movement of the user's body while ambulating or running on the treadmill surface and the lateral displacement rotational means allows lateral displacement of the body center of mass.

In a preferred embodiment, front body support 56 has a padded, flat or slightly contoured surface for contact with the user's body. In a preferred embodiment, the bottom edge 56b of the front body support is adjusted to contact against the pubic bone of the user and the top edge 56a of the front body support 56 is generally positioned in the waist area of the user.

In a preferred embodiment, the seat is adjusted so that the seat front 52a is tilted slightly downward with the seat back 52b tilted correspondingly upward as shown, for example, in FIG. 7 and FIG. 9. The seat and front body support form an angle less than ninety degrees. The user fits into this space defined by the less than ninety degree angle. The user, when positioned upon the seat which is tilted in this downward direction, is wedged against the front body support which swivels to firmly contact the body of the user. The seat back 52b, with its broad width, is in a raised position supporting the posterior of the user while the user is snugly wedged against the front body support 56 which supports the pelvic area of the user. Thus, the user is aided in maintaining his or her body position, posture and balance as the user sits, stands, ambulates or runs while the user is positioned in the treadmill body support system and on the treadmill surface. The body position, posture and balance is further maintained by the preservation of the angle of the seat and front body support relative to the treadmill surface as the center of gravity of the user moves up and down as the user walks or changes from a standing to a sitting position or vice versa.

In an alternative embodiment front body support 56 can be shaped to support the abdomen or chest of the user, and may include arm supports and arm rests.

In an alternative embodiment straps can be provided which are attached at either or both of front body support 56 and seat 52 and wrap around the user to provide additional support and balance.

Figure 6:
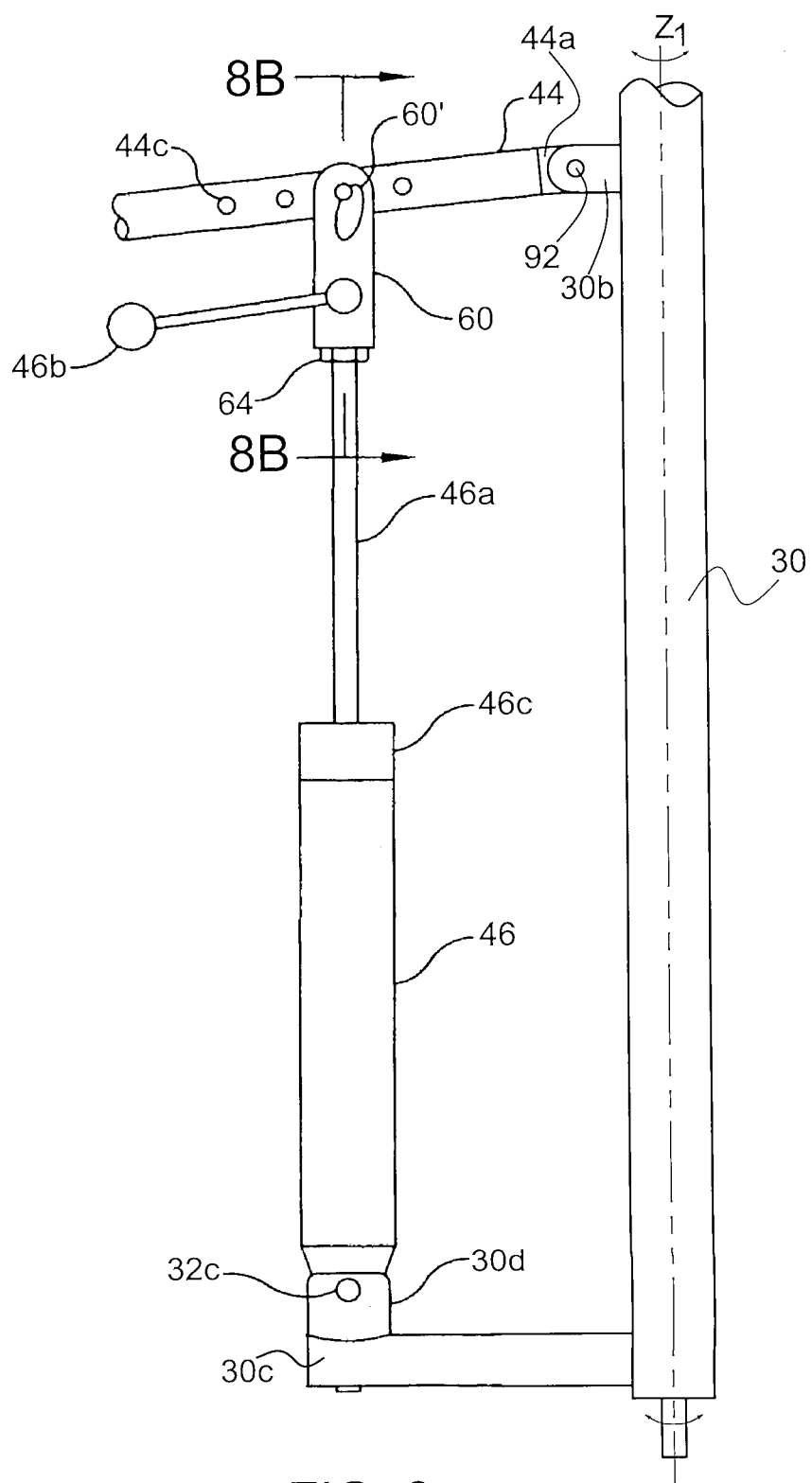
FIG. 6 is an enlarged partial right side view of the body weight support spring means with its connections at both ends in the treadmill body support system shown in FIG. 2(a).

Referring to FIG. 6, in a preferred embodiment, the body weight support spring means comprises a gas spring or a charged preloaded gas-charged cylinder 46 (also referred to as gas cylinder 46). The gas cylinder is provided with a piston rod 46a extending upward towards "U" shaped connector 60.

Figure 8A:
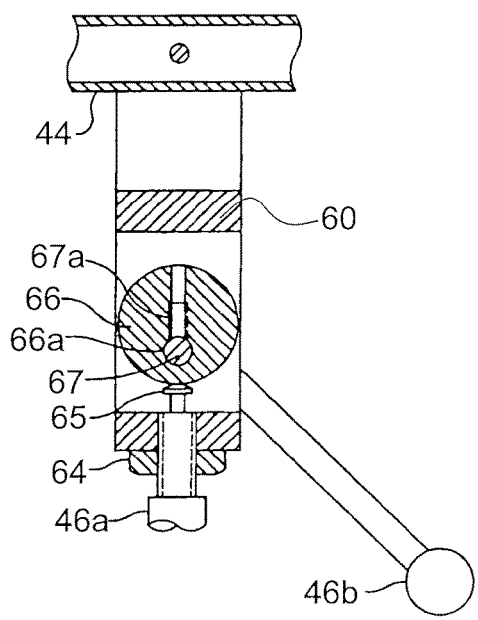
FIG. 8(a) is a section view of a part of the body weight support spring means including the piston rod, "U" shaped connector, off-center disk, compression pin and control lever in the directions of the arrows 8A-8A in FIG. 8(b).
Figure 8B:
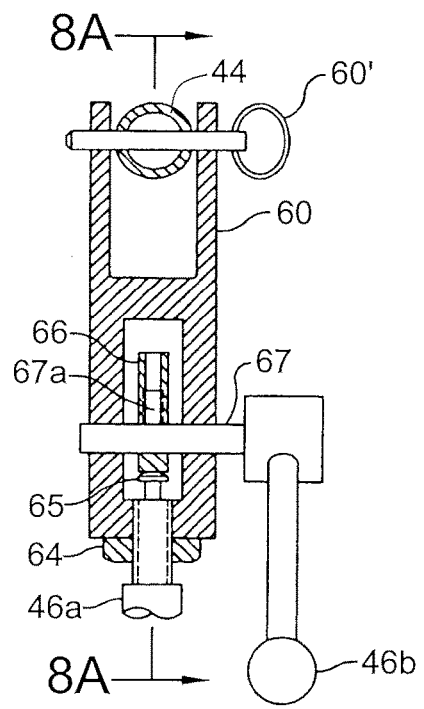
FIG. 8(b) is a section view of a part of the body weight support spring means including the piston rod, "U" shaped connector, off-center disk, compression pin and control lever in the directions of the arrows 8B-8B in FIG. 6.

Referring to FIG. 8(a) and FIG. 8(b) along with FIG. 6, the "U" shaped connector 60 houses an off-center circular disk 66 through which a control lever shaft 67 passes. The "U" shaped connector has openings to allow the passage of the control lever shaft 67 through the sides of the "U" shaped connector to contact the off-center circular disk 66. As depicted in FIG. 8(a) and FIG. 8(b) an end of piston rod 46a is positioned adjacent to the gas control pin 65 within the "U" shaped connector 60. A stabilizing piston rod nut 64 is positioned around the piston rod 46a where piston rod 46a is connected to the "U" shaped connector 60. The stabilizing piston rod nut 64 securely limits any rotational or horizontal sideways movement of the piston rod while permitting the piston rod freedom of movement into and out of the gas cylinder. The "U" shaped connector 60 is connected to the support lever 44 by an adjustment pin 60' with loop to facilitate the removal or insertion of the pin into any one of the several regularly spaced-apart openings 44c along the support lever 44. In the illustrated embodiment, as shown in FIG. 6, gas cylinder 46 is rotationally connected to rotational shaft 30 via rotational shaft offset 30c via rotational connector 30d and secured by rotational pin 32c. The gas cylinder can pivot rotationally about the rotational connector 30d and rotational pin 32c (about a Y-axis) as the "U" shaped connector 60 and adjustment pin 60' with loop are positioned at selected locations along the spaced-apart openings 44c of the support lever and locked into place at one of the spaced-apart openings as shown in FIG. 6.

The gas cylinder and piston rod may be reversed in their orientation so that the gas cylinder may be connected to support lever 44 by the adjustment pin 60' which is inserted into one of the spaced-apart openings 44c. In this reverse orientation piston rod 46a is rotationally connected to rotational shaft offset 30c by the "U" shaped connector 60. In this reversed orientation the "U" shaped connector is rotationally connected to rotational shaft offset 30c by rotational pin 32c which is inserted into rotational connector 30d. In this reverse orientation the gas control pin 65 can be compressed or released by means of cable wires. The cable wires can be activated by hand or foot to rotate the off-center disk 66 directly or to rotate the control lever shaft 67 which in turn rotates the off-center disk 66 to compress or release the gas control pin 65 to lock or unlock the body weight support means.

The gas cylinder's connection to the rotational shaft offset 30c, as generally shown in FIG. 2(a) through FIG. 5, is positioned so that the body weight support spring means is approaching a perpendicular angle to support lever 44 or is positioned to minimize the deviation from a perpendicular angle of the angle formed between the lengthwise axis of the body weight support spring means and the support lever. The maintenance of a perpendicular angle, or close to a perpendicular angle, allows for the transmission of the supporting forces with maximum efficiency and with minimal negation of the mechanical advantage obtained as the distance increases between the pivot point of the support lever 44 at the connection with rotational shaft 30 and the support lever's connection with the spring means at the "U" shaped adjustment pin 60'.

Connecting the body weight support spring means at different locations with adjustment pin 60' along support lever 44 at one of the openings 44c will result in a varied body weight supporting force or unweighting force applied to support lever 44, seat 52 and the user positioned in the treadmill body support system. As the distance between the pivoting axis of the support lever at the connection with rotational shaft 30 and the connection of the body weight supporting spring means into one of the openings 44c along support lever 44 with adjustment pin 60' increases, the mechanical advantage of the force supplied by the body weight support spring means (comprising gas cylinder 46 in one example) increases.

In a preferred embodiment the placement of the "U" shaped connector 60 and adjustment pin 60' along the support lever in a direction toward the seat will result in a greater support force imparted to the seat and the user while placement toward the rotational shaft 30 will result in a lesser support force imparted to the seat and the user. The amount of supporting force desired to be exerted upon the seat, and thereby the user positioned upon the seat, can be adjusted depending on the weight of the user and the degree of weight support assistance the user requires while ambulating or running on the treadmill surface, standing stationary on the treadmill surface, or in the seated position in the treadmill body support system while on the treadmill surface.

In an alternative embodiment, the location of the connection between support lever 44 and the body weight support spring means can be moved and locked into place by a turning screw mounted on rotational shaft 30 which moves the support lever toward or away from the rotational shaft by a threaded sleeve which is mated with grooves inside the support lever. Turning the screw will adjust the support force imparted to the seat and the user.

In the illustrated embodiment shown in FIG. 6 the body weight support spring means comprises gas cylinder 46 into which piston rod 46a retracts into or extends out of. The gas cylinder is preloaded with pressurized gas which is held in sealed chambers within the cylinder. Depending on a particular user of the treadmill body support system, the gas cylinder can be changed to provide a supporting force that fully supports or partially supports the particular user's supporting weight requirements. For example, different gas cylinders can be employed to accommodate children or those weighing less than 100 pounds to those weighing over 300 pounds. Additionally when a particular user's weight support needs change as the user becomes stronger or weaker the gas cylinder can be changed to provide the appropriate amount of support required.

Figure 10:
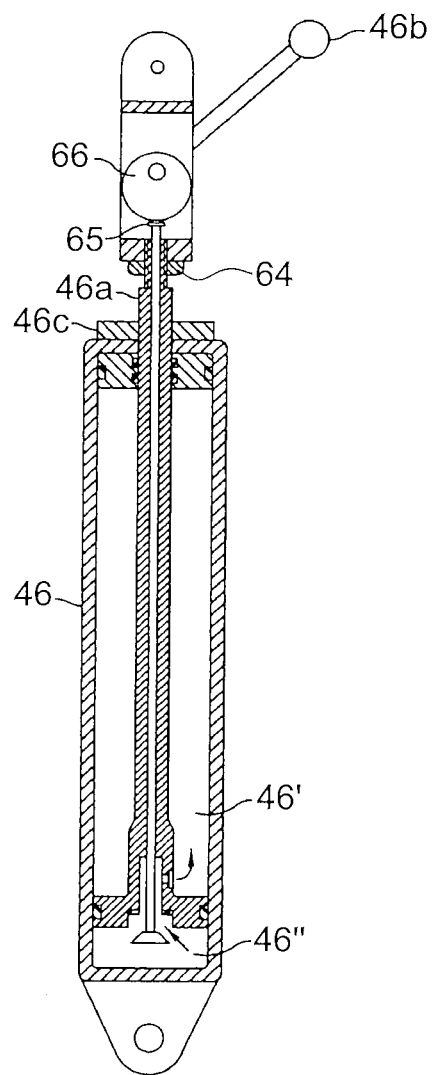
FIG. 10 is a vertical section view of the body weight support spring means shown in FIG. 6 at a right angle to the section 8B-8B shown in FIG. 6 in its preferred embodiment of a pressurized gas cylinder in its activated (dynamic mode) position allowing for movement of the pressurized gas within the chambers of the gas cylinder as illustrated by the arrows between upper interior chamber 46' and lower interior chamber 46".

The gas cylinder has control lever 46b as illustrated in FIG. 8(a) and FIG. 8(b). Control lever shaft 67 is connected to control lever 46b at one end and extends at its other end onto the surface of, or through an opening 66a, of off-center circular disk 66. The contact point of control lever shaft 67 onto the surface of the off-center circular disk 66 or opening 66a of the off-center circular disk 66 is not at the center point of the off-center circular disk 66 but rather is at an off-center location of the disk 66. A locking screw 67a clamps down the control lever shaft 67 to the off-center circular disk 66. When moved, the control lever 46b travels in a circular arc which rotates the control lever shaft 67 which in turn rotates the off-center circular disk 66. As the off-center circular disk rotates in an off-center fashion it will either compress or release the gas control pin 65. When the control lever is turned to an activated release (dynamic mode) position, the off-center circular disk moves the gas control pin 65 disposed adjacent to, and in physical contact with, the off-center circular disk 66. Upon activation, the gas control pin's movement releases the pressurized gas for movement within the sealed chamber of the gas cylinder as shown in FIG. 10. The pressurized gas exerts a force upon the piston causing the piston to extend out from the gas cylinder. When the pressurized gas is available to move within the chambers of the sealed gas cylinder the piston can move within the cylinder in response to the force applied by the user. As a result the seat assembly and user can move in an up or down direction and can provide partial body weight bearing support.

When the user desires to immobilize the seat from up and down movement, or desires full body weight support, control lever 46b is rotated so that the off-center circular disk 66 releases the pin from the activated position to a closed or locked (static mode) position. In the closed or locked positioned pin 65 limits the movement of the gas within the gas cylinder as shown in FIG. 11. In the locked rigid position, the piston rod 46a is immobilized and will not retract into or extend from the gas cylinder in response to the body force applied by the user of the treadmill body support system. Thus the support lever and seat assembly which are supported by the gas spring's position are likewise maintained in a fixed stationary position.

When the control lever 46b is turned to the activated released (dynamic mode) position, the pressurized gas transmits its force through the piston rod to provide partial body weight bearing support to the user or in some circumstances full body weight bearing support. The user of the treadmill body support system with the aid of partial body weight support can exert his or hers own variable body force by muscular effort in the legs and torso to support running, ambulating or standing efforts on the treadmill surface. The user can let his or hers body weight push seat 52 down against the gas spring's supporting force to an elevation desired for sitting or for transferring to a wheelchair positioned behind or over the treadmill surface and then lock the gas spring into place. This allows the user to slide off seat 52 into the wheelchair positioned on or over the treadmill surface with the seat in a fixed stationary position and without the seat exerting an upward force upon the user and without the risk of destabilizing the user.

In general the user can turn control lever 46b to the locked (static mode) position whenever the user desires to rest on the treadmill surface whether in a standing, partially standing, or in a treadmill exercising phase or when transferring to a wheelchair. Similarly when transferring from a sitting or resting phase the user can turn the control lever to the activated release (dynamic mode) position when the user desires partial weight bearing support to lift himself or herself to a standing or partially standing position and intends to use his or hers own efforts to the extent he or she is able for treadmill exercise, standing, moving or to partially support himself or herself on his or hers legs. The user can switch control lever 46b back and forth between the released and locked positions and move from a sitting to a standing or partially standing position which is either in a locked fully supported phase or a dynamic partial weight support phase and is not simply letting the seat passively support him or her on the treadmill surface.

The user positioned on seat 52 can transition from a standing to a sitting position by letting his or hers weight gradually lower himself or herself while receiving partial weight bearing support from the body weight support spring means 46. The user can then turn control lever 46b to the locked position while sitting on the seat 52 of the treadmill body support system and slide off onto a wheelchair positioned behind or over the treadmill surface. The user can transfer from the wheelchair to an upright standing position on the treadmill surface by sliding from the wheelchair onto seat 52 and activating control lever 46b to lift the body into a standing or more upright position.

The user can move the seat to numerous different elevations by activating control lever 46b and letting more or less of his or hers body weight rest upon the seat. The height of the seat and the position of the user whether in a standing, sitting or partially standing position on the treadmill surface can be changed in any desired varied, random or repeated sequence. The amount of weight supporting force the user experiences can be adjusted without changing the gas cylinder by sliding the body weight support spring means along the support lever 44 either farther from, or closer to, the fulcrum point of the support lever's rotational connection to the rotational shaft 30.

If the user experiences an uncontrolled or sudden weakening on the treadmill in the body support system so that the legs cannot support the user when control lever 46b is in the activated position and the gas cylinder or body weight support spring means is providing partial weight bearing support, stop limiting means 46c are provided. The stop limiting means can consist of a stop collar or stop block made from a cushioned force absorbing material. The stop limiting means will arrest the downward movement of the seat to a pre-determined elevation off the treadmill surface in a fixed down position of the seat to keep the user from falling and contacting the treadmill surface.

One method of using the treadmill body support system is as follows. The user can mount and position his or hers body in the seat assembly of a treadmill body support system from a standing position or from a wheelchair positioned over or on a treadmill surface, for example, by adjusting the seat to a stationary sitting height position by movement of the control lever to the static mode position when the treadmill body support system is in the treadmill body support sitting height position. Positioning of the wheelchair over the treadmill surface can be accomplished by providing a wheelchair ramp that straddles over the treadmill surface. When the user has positioned his or hers body in the seat assembly of the treadmill body support system with the pelvis between seat 52 and front support 56 the user is conveniently and safely positioned in the treadmill body support system.

The user, or user support personnel positioned next to the treadmill and body support system, can place control lever 46b in the dynamic mode position which will free the piston and give upward body support force to assist the user in standing on the treadmill.

In the standing position on the treadmill the user can exercise in dynamic standing with lateral gait displacement; bending knees, stretch further up on the tip of the toes, or weight shift between left and right legs while the user is safely positioned in the treadmill body support system. If the user needs to rest, the user, or support personnel, can lock the piston and sit in the standing position on the treadmill in the treadmill body support system.

When the user is ready to ambulate on the treadmill surface, the user, or support personnel, can place control lever 46b in the dynamic mode position and adjust the treadmill surface speed to the desired value. The user can ambulate on the treadmill surface with supported body, including the pelvis, and will move up and down to establish a vertical gait displacement of the body center of mass while supported and with reduced body force on the treadmill surface, and will move left and right as the body shifts weight between the right leg and left leg to establish a lateral gait displacement while still supported as allowed by rotation of lateral displacement rotational means 30 interaction with the other components of the treadmill body support system.

Due to the absence of side components in the treadmill body support system, user support personnel have unimpeded access to assist and guide the user positioned in the body support system from either side of the body support system either by manipulation of the user's body parts, operation of control lever 46b, or other adjustments to the treadmill body support system.

When the treadmill exercise has been completed, the user can return to the sitting position in the treadmill body support system and easily transfer, for example, with backwards motion to a wheelchair that has been rolled up behind the user on a wheelchair ramp. While the term wheelchair is used to describe the transfer device with the treadmill body support system, the transfer device may also be variants of a wheelchair, such as a standing wheelchair, knee scooter or other assisted mobility device used to transfer an impaired or disabled individual from one location to another.

Figure 13:
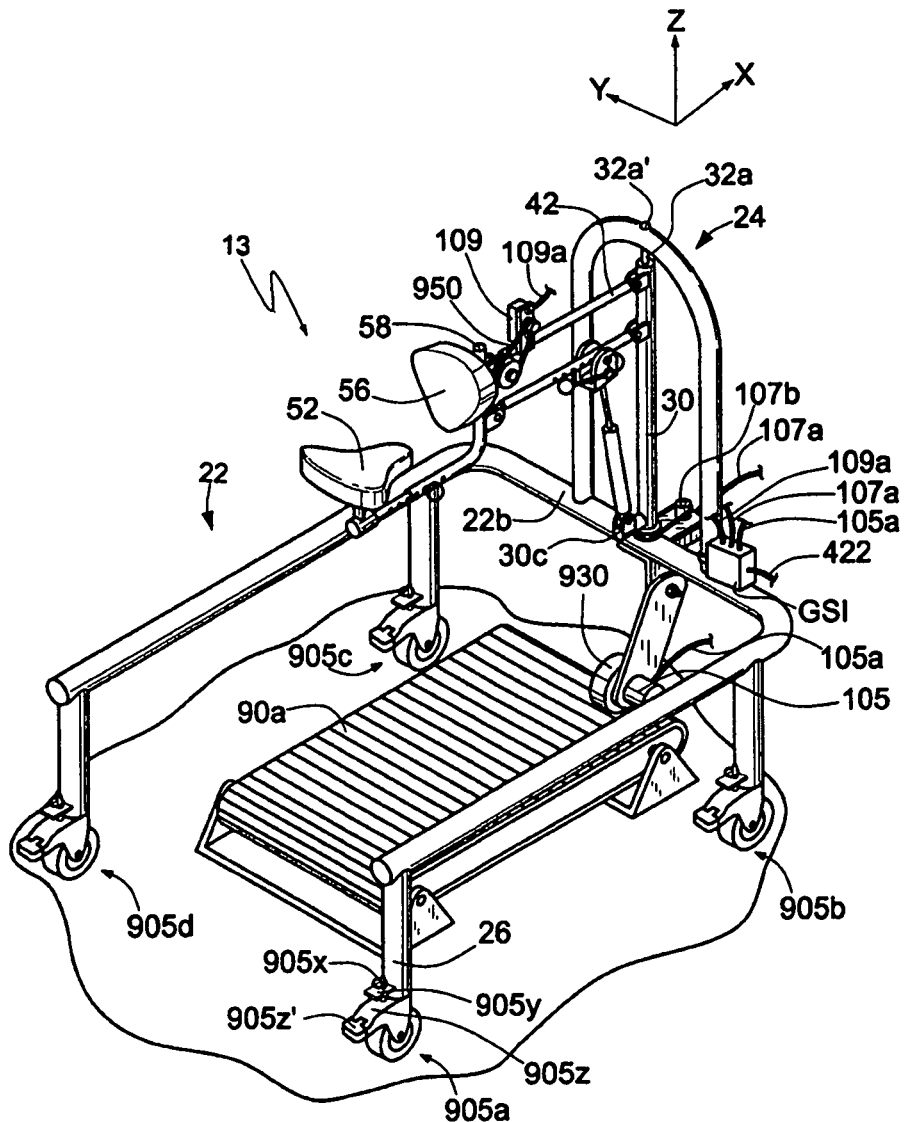
FIG. 13 is a perspective view of one example of a gait analysis system of the present invention used with a body support system having a user-adjustable body weight support during gait training exercise and analysis over a fixed surface.

There is shown in FIG. 13 one example 13 of the present invention where a gait analysis system is combined with a body support system having a user-adjustable body weight means that is used with a treadmill. The body support system 10 shown in FIG. 2(a) is modified as follows for a gait analysis system with body support system 13 of the present invention.

In the example of FIG. 15 four locking swivel casters 905a-905d can be used in the unlocked position to move the treadmill body support system in position over treadmill surface 90a and can then be aligned and locked when the treadmill body support system is in the proper position over the treadmill surface. In this embodiment of the invention alignment of each caster is accomplished as illustrated for swivel caster 905a by placing caster alignment pin 905x with top ring end through the hole in caster alignment key 905y fixed to frame leg 26 with the opposing free end of pin 905x inserted into an indentation in caster fender 905z. Locking is accomplished by moving caster tab 905z' from the unlocked position to the locked position.

A forward (X) gait measurement (or directional distance) sensor is provided to measure the distance treadmill surface 90a moves over a time period when a user is walking over the treadmill surface while positioned in the body support system. In this example the forward X-direction distance sensor is X-rotary encoder 105 as best seen in FIG. 15(b). The output shaft (not seen in the drawings) of the X-rotary encoder is rotationally fixed to the axle of X-direction wheel 930 that rotates in the X-direction with the treadmill surface. In this example X-rotary encoder 105 has X-encoder cable 105a suitably connected to gait sensors integrator (GSI), which in this example of the invention, is a GSI enclosure suitably fixed to base foot 22b of "U" shaped frame base 22. Pivot arm 932 in this example of the invention is attached at opposing ends to base foot 22b of "U" shaped frame base 22 (via pivot arm 932 and X-angle bracket 934) and X-rotary encoder 105 with free rotation of the output shaft of X-rotary encoder. Locking means 936, which in this example comprises a screw and nut, locks the X-direction wheel in a position where it maintains constant non-slip contact with treadmill surface 90a as it moves in the X-direction.

Figure 15A:
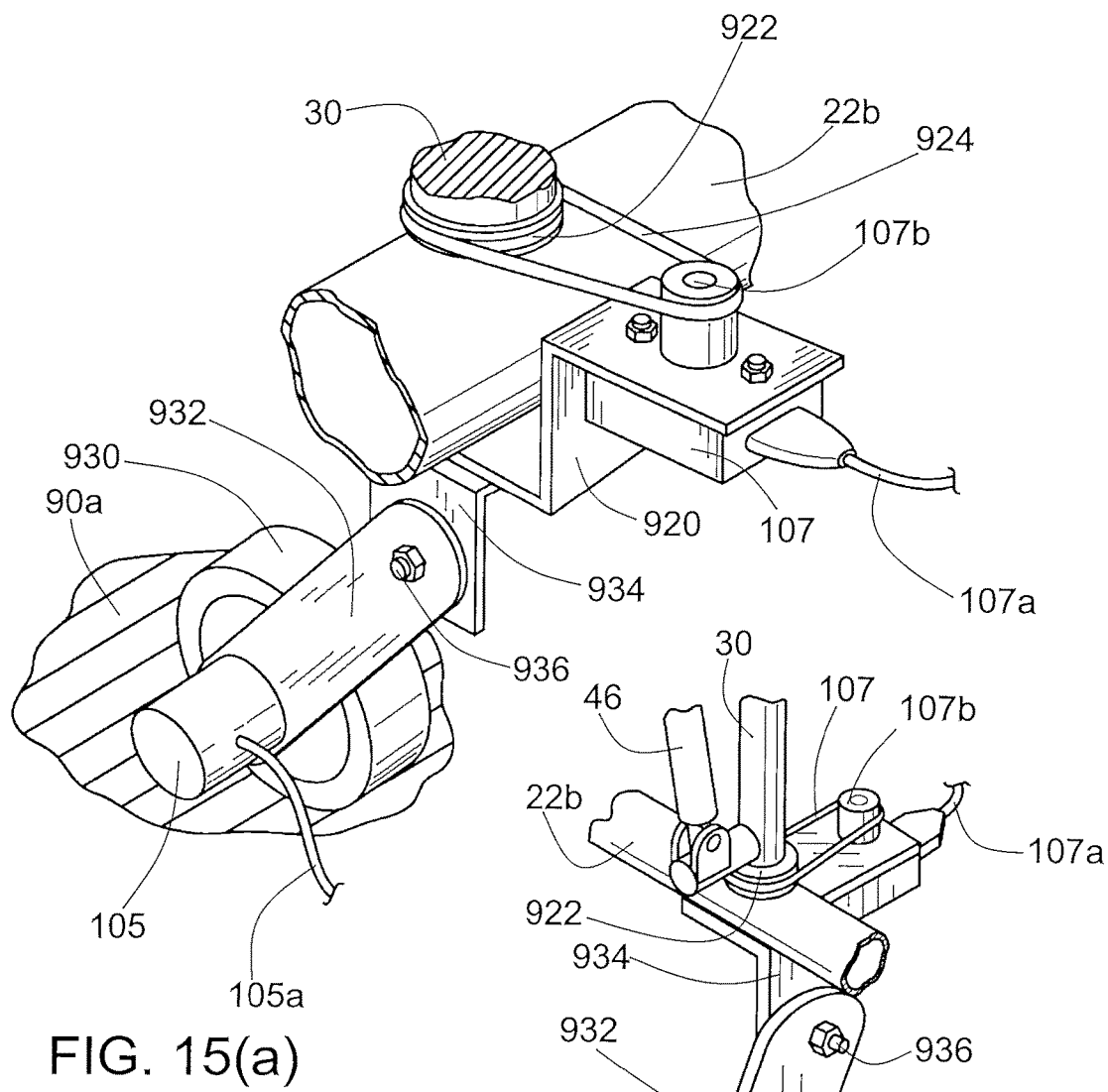
FIG. 15(*a*) is a detail view of one example of a lateral (Y) direction gait measurement sensor used to measure Y distance over a time period for the gait analysis system shown in FIG. 13 or FIG. 14.
Figure 15B:
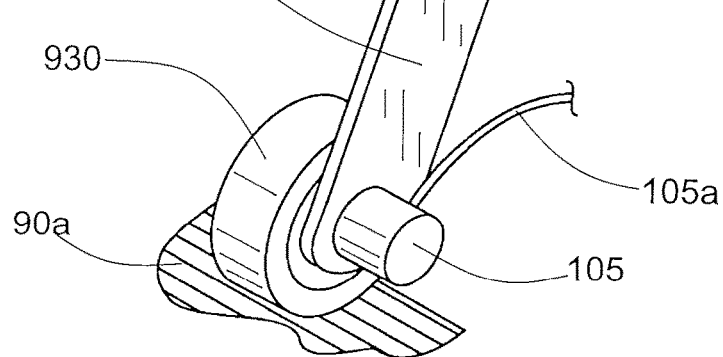

A lateral (Y) gait measurement (or directional distance) sensor is provided in this example of the invention to measure the distance that lateral displacement rotational means 30 rotates as shown for example in FIG. 15(a) and FIG. 15(b) with the rotational angle being proportional to the lateral gait distance of the user of the body support system. In this example the lateral (Y) direction distance sensor is Y-rotary encoder 107 as best seen in detail FIG. 15(a). Y-rotary encoder is suitably fixed to base foot 22b of "U" shaped frame base 22 in this embodiment by Y-angle bracket 920 which is suitably fixed at opposing ends to base foot 22b and Y-rotary encoder 107. In this example Y-rotary encoder 107 has Y-encoder cable 107a suitably connected to the GSI enclosure. Annular ring 922 is fixed to the bottom end of lateral displacement rotational means 30 and has an annular groove around its outer circumference for fitting of drive belt 924 which belt is also suitably fitted around Y-encoder output shaft 107b so that rotation of the lateral displacement rotational means 30 drives rotation of Y-encoder output shaft 107b by an angle proportional to the angle of rotation of the lateral displacement rotational means. The angle of rotation of the Y-encoder's output shaft proportionately corresponds to gait distance in the lateral Y-direction.

Figure 15C:
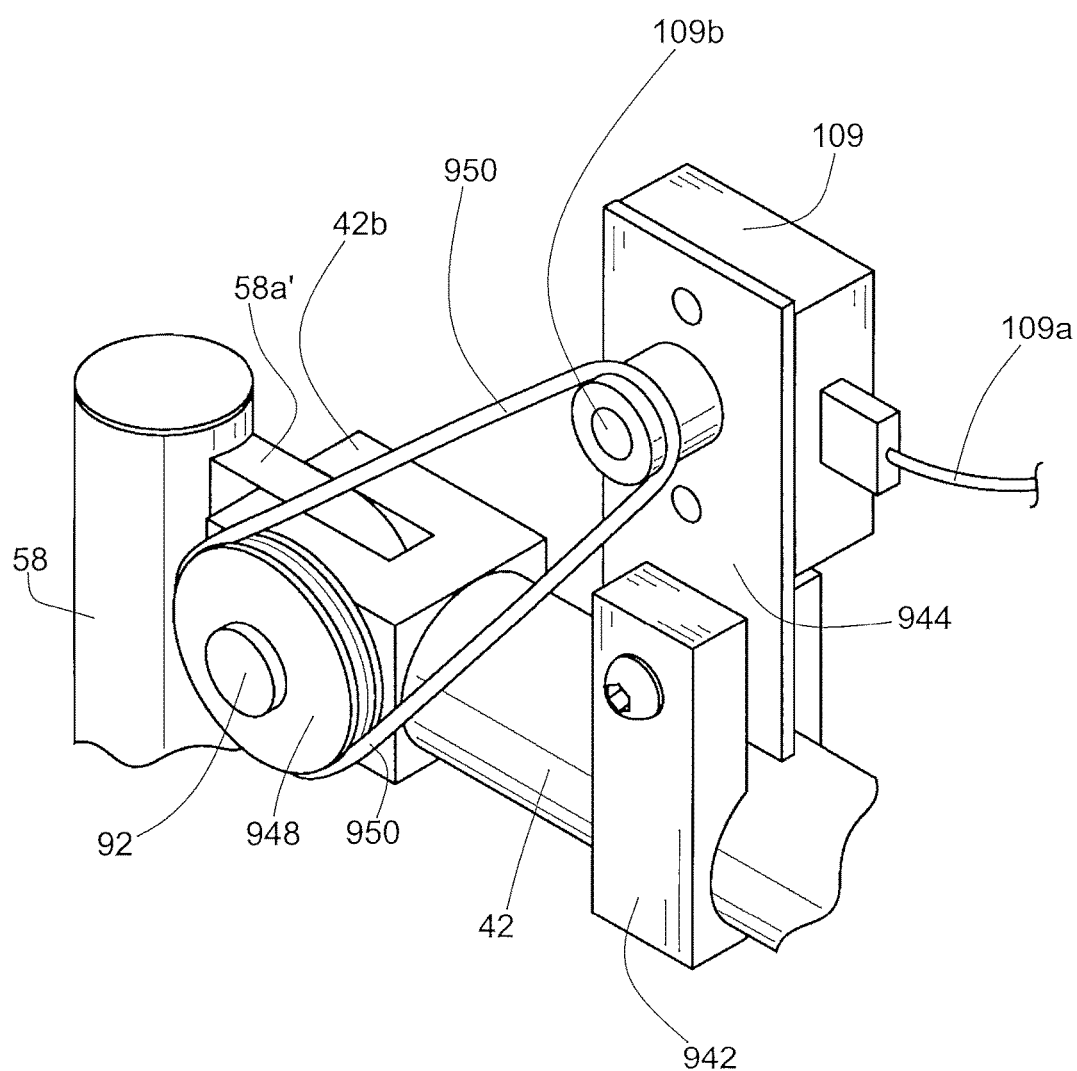

A vertical (Z) gait measurement (or directional distance) sensor is provided to measure the distance that stabilizing arm opposing end 42b of position stabilizing arm 42 rotates as the user moves in the upward or downward direction with the rotational angle being proportional to the vertical gait distance of the user of the body support system. In this example the vertical distance sensor is rotary encoder 109 as best seen in FIG. 15(c) that is suitably fixed to position stabilizing arm 42 via Z-encoder bracket 944 which is fixedly retained in "U" saddle bracket 942 that is fixedly attached to the position stabilizing arm 42. In this example Z-rotary encoder 109 has Z-encoder cable 109a suitably connected to the GSI enclosure. Fastener 92 in this embodiment of the invention is fixed through horizontally aligned holes in "U" shaped position stabilizing arm end 42b while being rotatable around front body support post connector 58a' that is inserted in the "U" shaped position stabilizing arm end 42. Fastener 92 is extended at one end so that Z-direction pulley 948 can be fixed to the extended end as shown in FIG. 15(c). Belt 950 is fitted in the groove of pulley 948 and around Z-encoder shaft 109b so that rotation of the position stabilizing arm 42 drives rotation of Z-encoder shaft 109b by an angle proportional to the angle of rotation of the position stabilizing arm. The angle of rotation of the Z-encoder's output shaft proportionately corresponds to gait distance in the vertical Z-direction.

In some embodiments of the invention only a forward and a vertical gait measurement sensor are used when the gait analysis system is combined with a body support system having a user-adjustable body weight means that is used with a treadmill; that is lateral directional distance is not used for these gait analysis systems.

Figure 14:
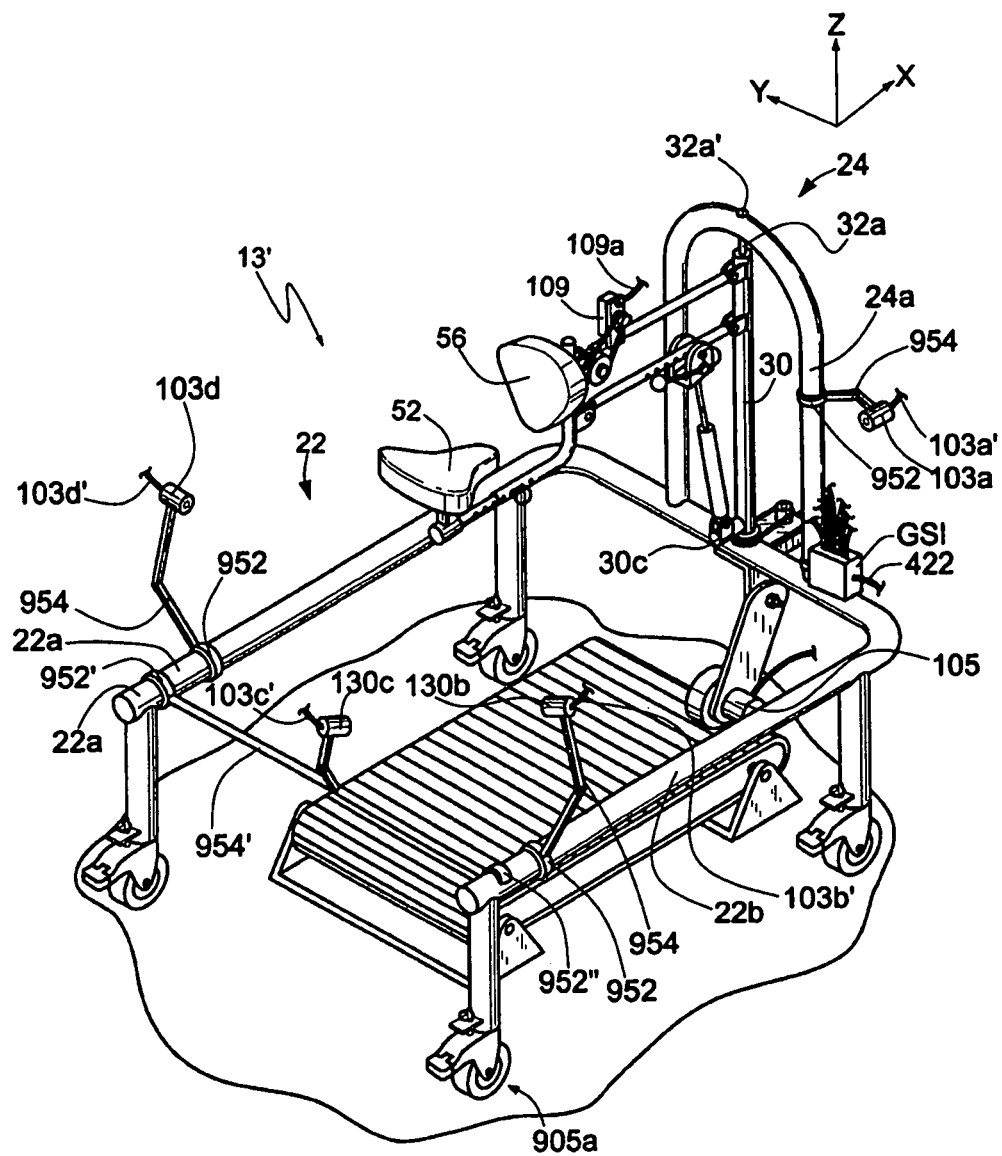
FIG. 14 is a perspective view of another example of a gait analysis system of the present invention used with a body support system having a user-adjustable body weight support during gait training exercise and analysis on a treadmill shown in FIG. 2(a) through FIG. 12(b).

Example 13' of the present invention shown in FIG. 14 is similar to that shown in FIG. 13 except that a gait visual sensor network is added to example 13 in FIG. 13. In example 13', the gait visual sensor network comprises at least one user forward (or front) camera 130a; at least one user right side 130b; at least one user rear camera 130c; and at least one user left side user camera 130d to record movement of the user during gait training and analysis on the body support system. One or more of the cameras may be removably mounted to the body support system, for example, by providing openable retaining rings 952 that fix each camera's connecting extension poles 954 to frame base 22 and frame bridge 24. The rear camera may optionally have an installed position and a user access position as shown in FIG. 14 in the installed position to allow the user to enter or exit the body support system from the rear of the body support system and treadmill, for example, by providing a means for connecting pole 954' to rotate about base arm 22a at pivotable retaining ring 952' with opposing end of connecting pole 954' having retaining ring 952" with a semicircular shape to allow upward rotation to a user access position for entry or exit. When a gait visual sensor network is provided, in this example of the invention, wired cables 103a', 103b', 103c' and 103d' are provided from the cameras to the GSI enclosure mounted on the body support system in FIG. 14.

In any embodiment of the invention where a gait visual sensor network is provided with one of the body support systems, the network comprises at least one visual sensor connected to the body support system. The one or more visual sensors can be video cameras operating in the visible light spectrum or a combination of visual sensors and infrared sensors to sense a user's body thermal profile. Generally the field of view of a gait visual sensor can be the entire view of the user's legs from foot contact with the treadmill or fixed surface up to the hips or a sub-region within this general visual field of view controlled manually by visual sensor positioning or remotely via an automated visual sensor positioning system.

Figure 16:
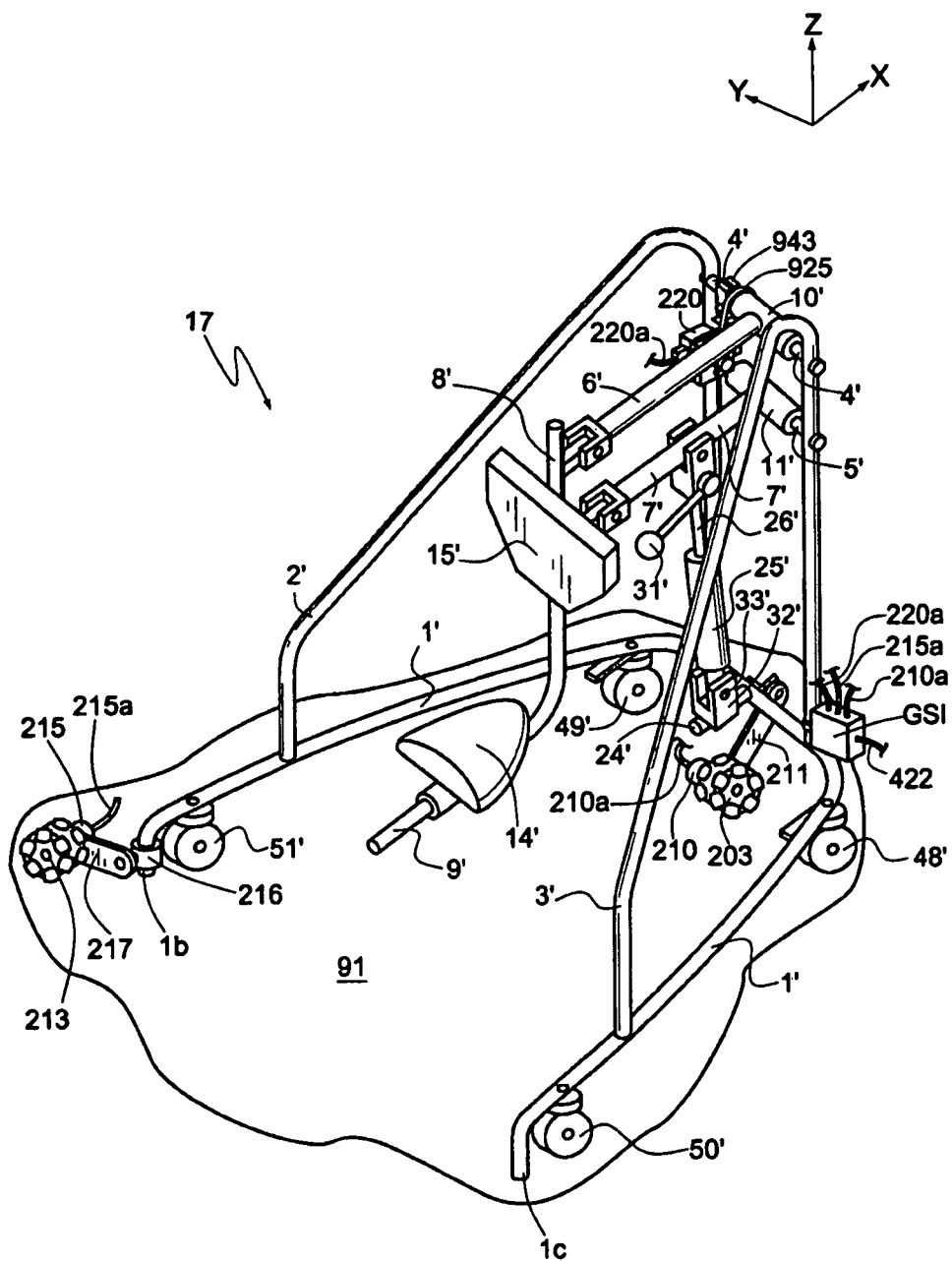
FIG. 16 is a perspective view of one example of a gait analysis system of the present invention used with a body support system having a user-adjustable body weight support during gait training exercise and analysis over a fixed surface.

There is shown in FIG. 16 one example 17 of the present invention where a gait analysis system is combined with a body support system having a user-adjustable body weight means that is used on a fixed (for example, ground) surface 91. The body support system may be a sit down and stand up walker with seat assembly as disclosed in U.S. Pat. No. 8,151,812 B2 which reference and disclosure is incorporated by reference herein in its entirety. Reference numerals used herein for the body support system in U.S. Pat. No. 8,151, 812 B2 are the reference numerals in U.S. Pat. No. 8,151, 812 B2 with a prime suffix added to the reference numerals.

Figure 17:
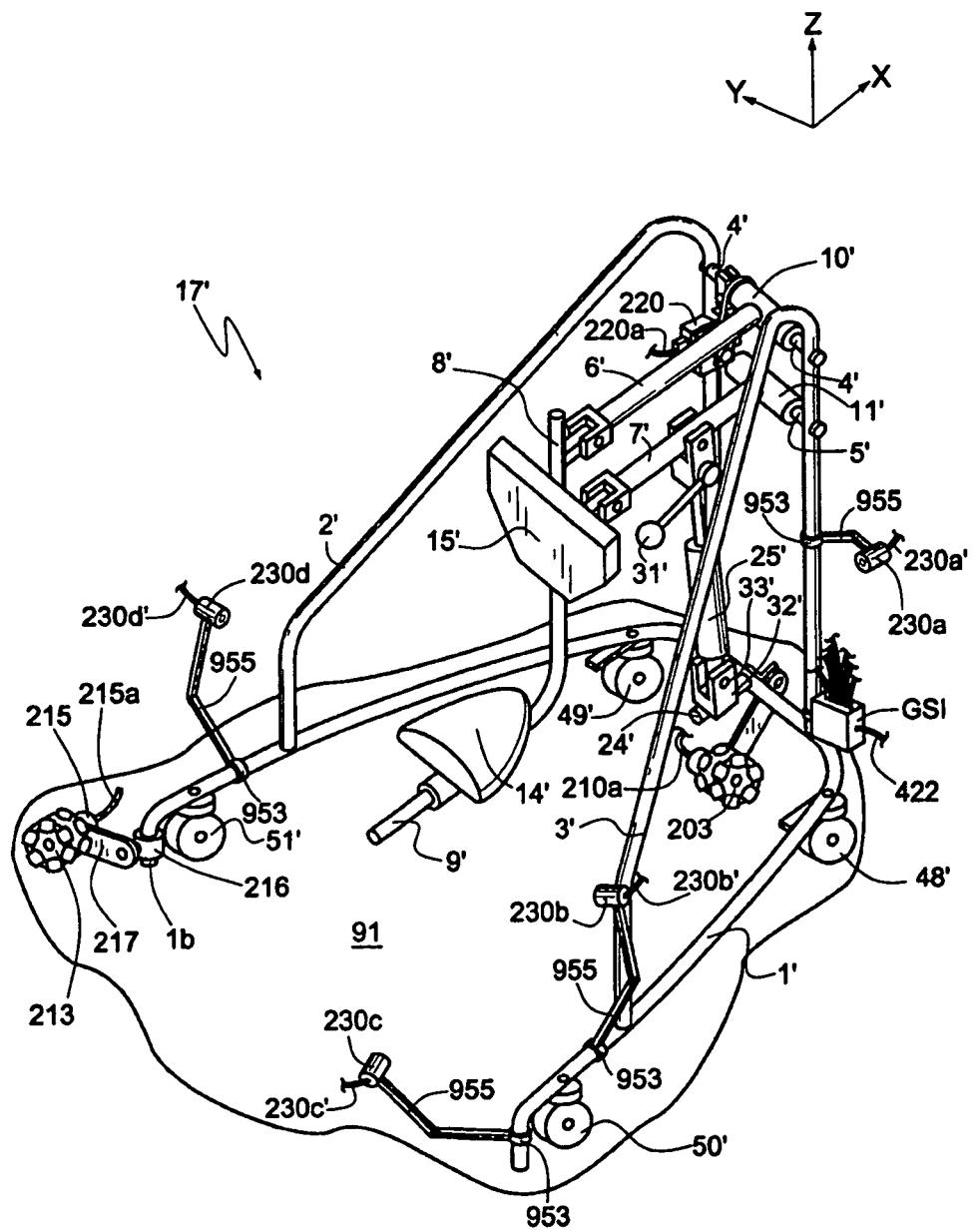
FIG. 17 is a perspective view of another example of a gait analysis system of the present invention used with a body support system having a user-adjustable body weight support during gait training exercise and analysis over a fixed surface.

As shown in FIG. 16 and FIG. 17 herein one embodiment of the body support system in U.S. Pat. No. 8,151,812 B2 has a support frame assembly with a frame base 1' and two arcuate side members 2' and 3', connected through two cross bars 4' and 5' and roller means 48', 49', 50' and 51' mounted on the support frame for contacting a ground surface 91 and rolling the frame. A support lever 7' extends between the support frame and a front body support post 8' and is connected rotationally at one end to the post 8' and connected rotationally at the other end to the support frame. A front body support 15' is mounted on the front body support post 8' by a swivel joint so that the front body support 15' can be tilted and can be adjustably positioned along the front body support post 8' up or down. The front body support 15' has a front planar surface. A seat 14' has a front end and a back end for supporting the user, with the seat mounted on a seat support extension 9' connected to the front body support post and wherein the front of the seat is positioned in a direction facing the front body support 15' and the support frame so that the seat positions the user to face the body support system to enable the user's body to push the body support system in front of the user and wherein the seat 14' can be adjustably positioned along the seat support extension closer toward or further away from the front body support and wherein the seat is adjustably tilted downward so that the user supported by the seat 14' will be wedged between the seat and front body support with the user's abdominal region in contact with the front body support. A position stabilizing arm 6' is positioned at an elevation higher than the support lever 7' and parallel to the support lever. The arm 6' extends between the front body support post and support frame and is rotationally connected at one end to the post 8' and rotationally connected at the other end to the support frame so that the seat 14 and front body support are maintained at a constant angle with respect to the ground surface 91 as the position stabilizing arm 6' and support lever 7' move rotationally about the support frame and post. Adjustable body weight support spring means is rotationally connected on the support frame for applying a full or partial weight-bearing supporting force to the support lever 7 so that the seat, front body support and user are able to move up or down responsive to the variable force supplied by the user as the user walks, stands or sits in the body support system for a gait analysis or exercise. A control lever 31 mounted on the adjustable body weight support spring means so that upon movement of the control lever an off center circular disk is turned which releases a gas control pin to limit the movement of a pressurized gas within the adjustable body weight support spring means so that the movement of the seat and front body support can be locked at variable fixed elevations including a sitting height position to allow a user to enter or exit the body support system from a sitting position and hold the seat, front body support and user in a continuous sitting position without the application of the user's body weight force or force by another person and so that upon further movement of the control lever 31 the off center circular disk is turned to activate the gas control pin to release the movement of the pressurized gas within the adjustable body weight support spring means so that the seat, front body support and user are released from a sitting position or fixed elevation to a standing or walking position supported by the adjustable full or partial body weight support spring means during a gait analysis of the present invention. The body support system disclosed in U.S. Pat. No. 8,151,812 B2 is modified as follows for a gait analysis system with a body support system of the present invention.

A forward (X) gait measurement (or directional distance) sensor is provided to measure the distance a user positioned in the body support system shown in FIG. 16 moves in the forward X-direction over fixed surface 91 in a time period. In this example the forward X-direction distance sensor is X-rotary encoder 210 as best seen in detail FIG. 18(b) as suitably fixed to front 1a of frame base 1'. In this example of the invention X-rotary encoder 210 is attached to front 1a of frame base 1' via X-support arm 211 and X-angle bracket 212 that is fixedly attached to support frame base extension 24', which in this example extends through front 1a while being fixedly attached to front 1a of frame base 1'. In this example forward X-omniwheel 203 is fixedly attached at one end of X-support arm 211 and is in contact with fixed surface 91 and rotates in the X-direction while allowing movement in other directions along the fixed surface. X-rotary encoder 210 is fixedly attached to one end of the X-support arm and has an X-rotary encoder output shaft 210b connected to the rotational axis of X-omniwheel 203 so that the X-rotary encoder output shaft rotates with omniwheel 203 only in the forward X-direction. X-rotary encoder 210 has a wired output 210a connected to GSI enclosure, which in this example of the invention, is suitably fixed to a side front of frame base 1'.

A lateral (Y) gait measurement (or directional distance) sensor is provided in some examples of the invention to measure the distance a user positioned in the body support system moves in the lateral Y-direction over fixed surface 91 in a time period. In this example the lateral Y-direction distance sensor is Y-rotary encoder 215 as best seen in detail in FIG. 18(c) as suitably fixed to one of the left or right rear legs 1b or 1c of frame base 1'. In this example of the invention Y-rotary encoder 215 is attached to the left rear leg 1b via a suitable clamping fixture 216 that is rotatably attached to one end of Y-support arm 217. In this example lateral Y-omniwheel 213 is in contact with fixed surface 91 and rotates with Y-omniwheel 213 in the Y-direction while allowing movement of the Y-omniwheel and the body support system in other directions along the fixed surface. In this example lateral Y-rotary encoder 215 is fixedly attached to the opposing end of Y-support arm 217 and has a Y-rotary encoder output shaft 215b connected to the rotational axis of Y-omniwheel 213 so that the Y-rotary encoder output shaft rotates with omniwheel 213 only in the lateral Y-direction. Y-rotary encoder 215 has a wired output 215a connected to the GSI enclosure.

Figure 18A:
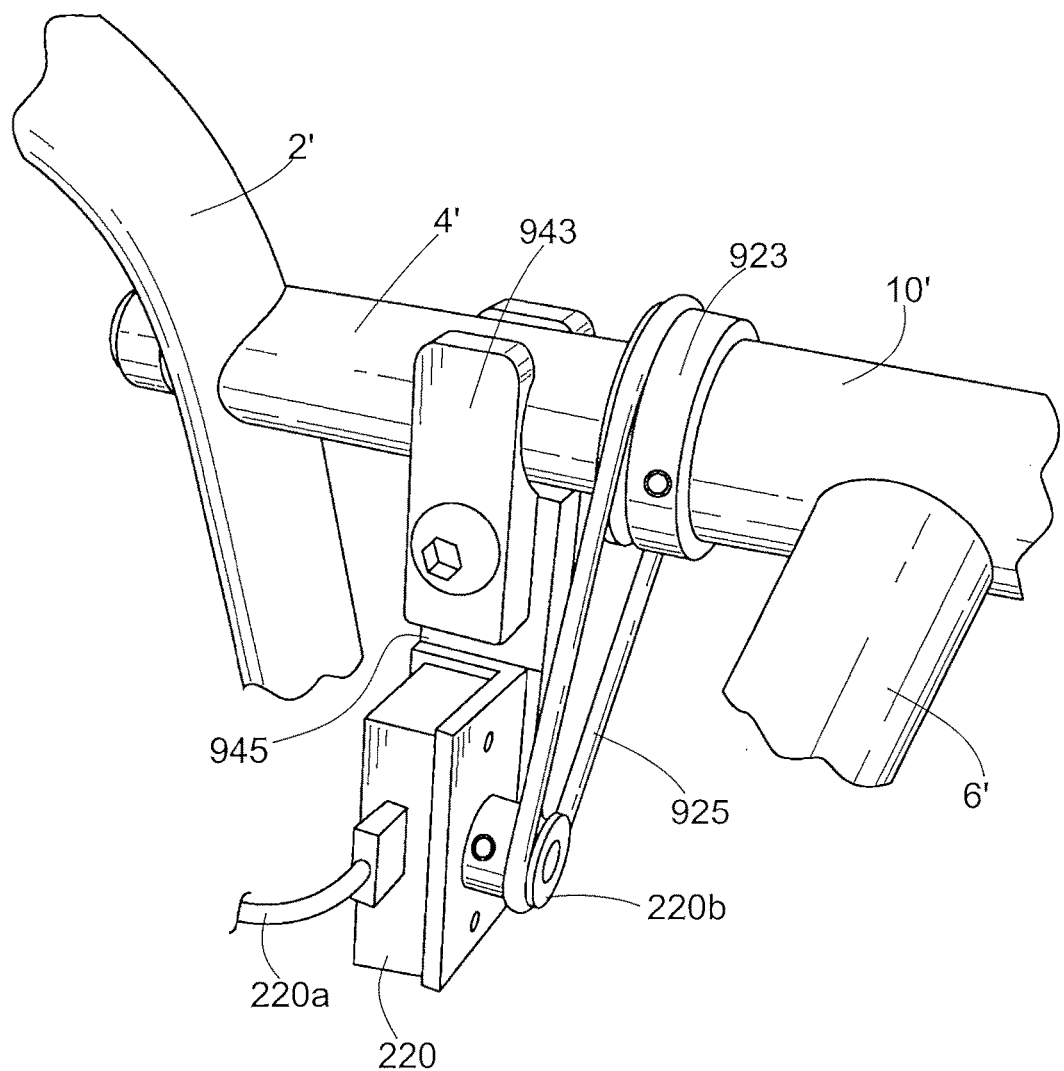
FIG. 18(*a*) is detail view of one example of a vertical (Z) direction gait measurement distance sensor used to measure Z distance over a time period for the gait analysis system shown in FIG. 16 or FIG. 17.
Figure 18B:
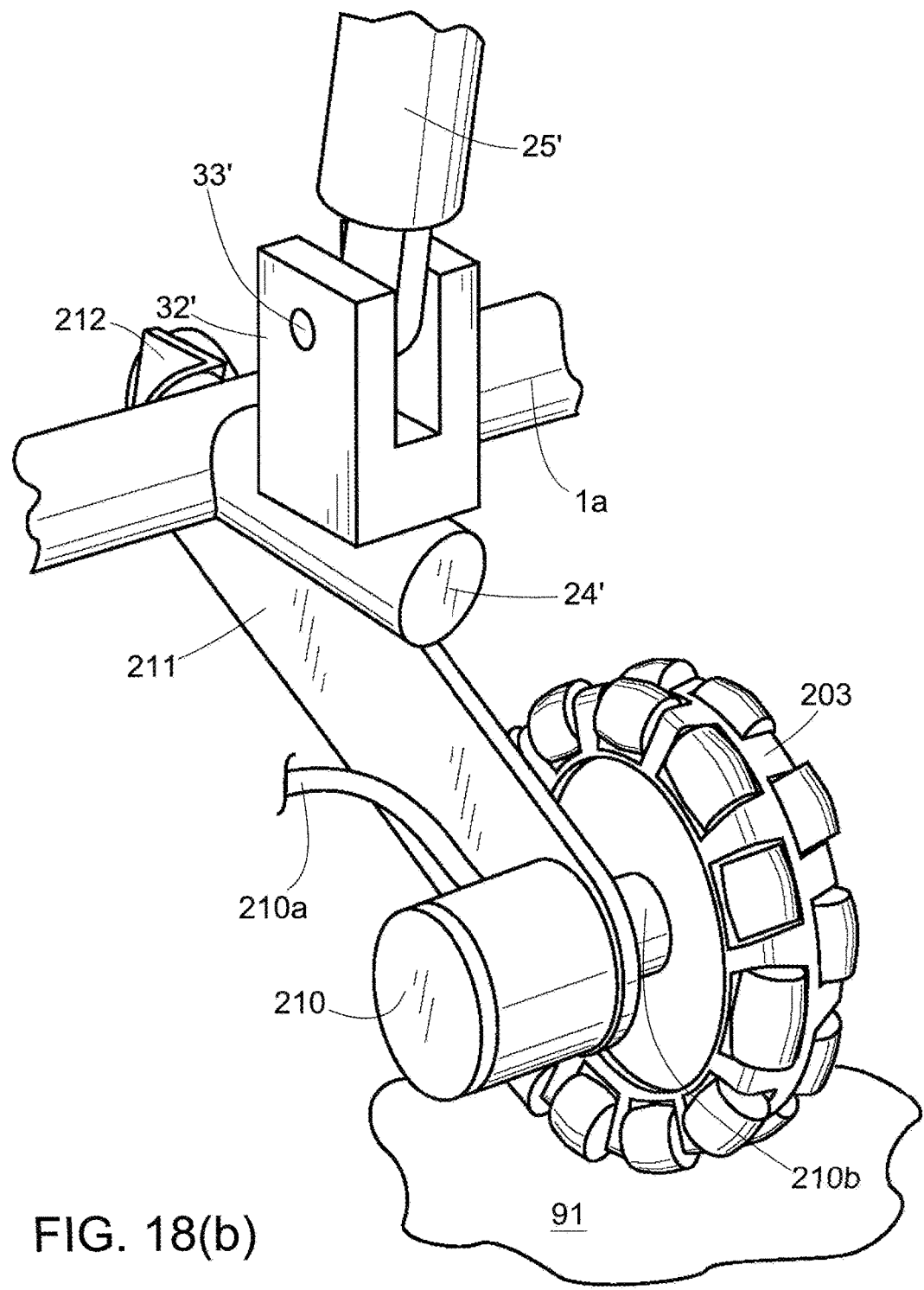
Figure 18C:
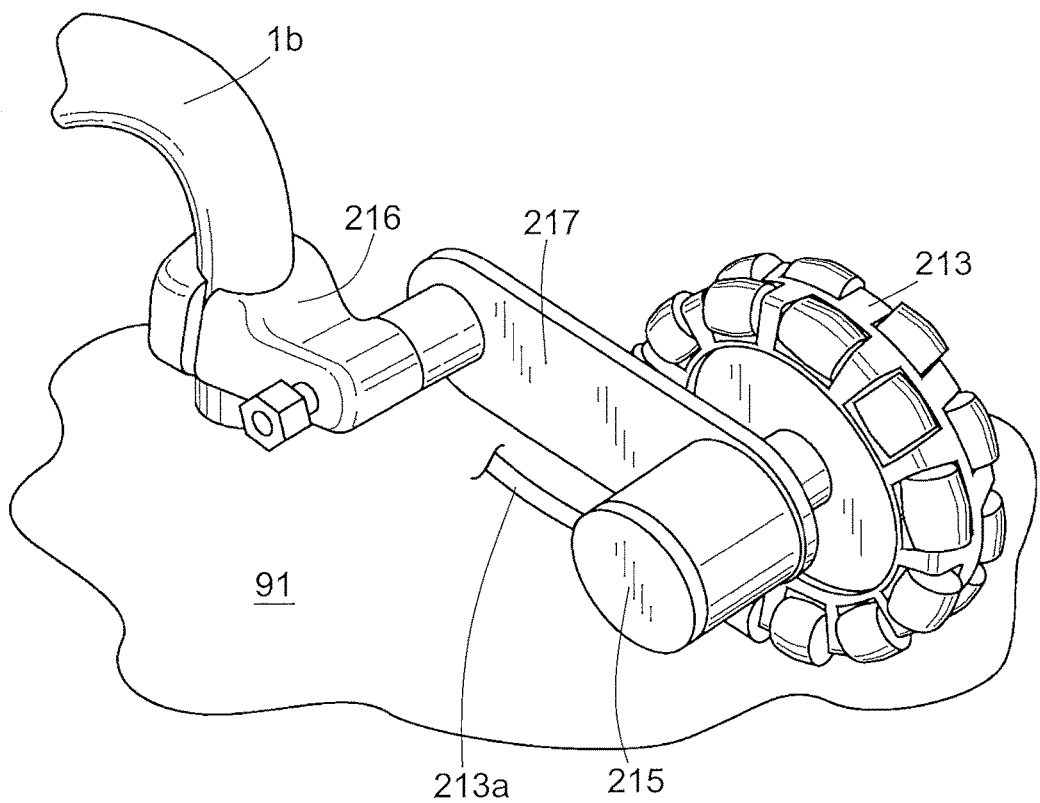

A vertical (Z) gait measurement (or directional distance) sensor is provided to measure the distance that sleeve connection 10' or 11' rotates relative to cross bar 4' or 5' respectively as the user moves in the upward or downward direction during ambulation on the body support system with the rotational angle being proportional to the vertical Z-direction gait distance of the user of the body support system. In this example the vertical Z-direction distance sensor is Z-rotary encoder 220 as best seen in FIG. 18(a) as suitably fixed to cross bar 4' and rotationally attached to sleeve connection 10'. In this example of the invention Z-rotary encoder 220 is suitably fixed to cross bar 4' via Z-encoder bracket 945 which is fixedly retained in "U" saddle bracket 943 that is fixedly attached to cross bar 4', In this example Z-rotary encoder 220 has Z-encoder cable 220a suitably connected to the GSI enclosure. Annular ring 923 is fixed around sleeve connection 10' and has an annular groove around its outer circumference for fitting of drive belt 925 which belt is also suitably fitted around Z-encoder output shaft 220*b* so that rotation of sleeve connection 10' around cross bar 4' drives rotation of Z-encoder shaft 220*b* by an angle proportional to the angle of rotation of sleeve connection 10'. The Z-encoder output shaft's angle of rotation proportionately corresponds to gait distance in the lateral Z-direction.

In some embodiments of the invention only a forward and a vertical gait measurement sensor are used when the gait analysis system is combined with a body support system having a user-adjustable body weight means that is used with on a fixed surface; that is lateral directional distance is not used for gait analysis.

Example 17' of the present invention shown in FIG. 17 is similar to that shown in FIG. 16 except that a gait visual sensor network is added to example 17 in FIG. 16. In example 17', the gait visual sensor network comprises at least one user forward (or front) camera 230*a*; at least one user right side 230*b*; at least one user rear camera 230*c*; and at least one user left side use camera 230*d* to record movement of the user during gait training and analysis on the body support system. One or more of the cameras may be removably mounted to the body support system, for example, by providing openable retaining rings 953 that fix each camera's connecting extension poles 955 to frame base 1' or arcuate side members 2' or 3'. When a gait visual system is provided, in this example of the invention, wired cables 230*a'*, 230*b'*, 230*c'* and 230*d'* are provided from the cameras to the GSI enclosure mounted on the body support system in FIG. 17.

In any embodiment of the invention where a gait visual sensor network is provided with one of the body support systems, the network comprises at least one visual sensor connected to the body support system. The one or more visual sensors can be video cameras operating in the visible light spectrum or a combination of visual sensors and infrared sensors to sense a user's body thermal profile. Generally the field of view of a gait visual sensor can be the entire view of the user's legs from foot contact with the treadmill or fixed surface up to the hips or a sub-region within this general visual field of view controlled manually by visual sensor positioning or remotely via an automated visual sensor positioning system.

Figure 19:
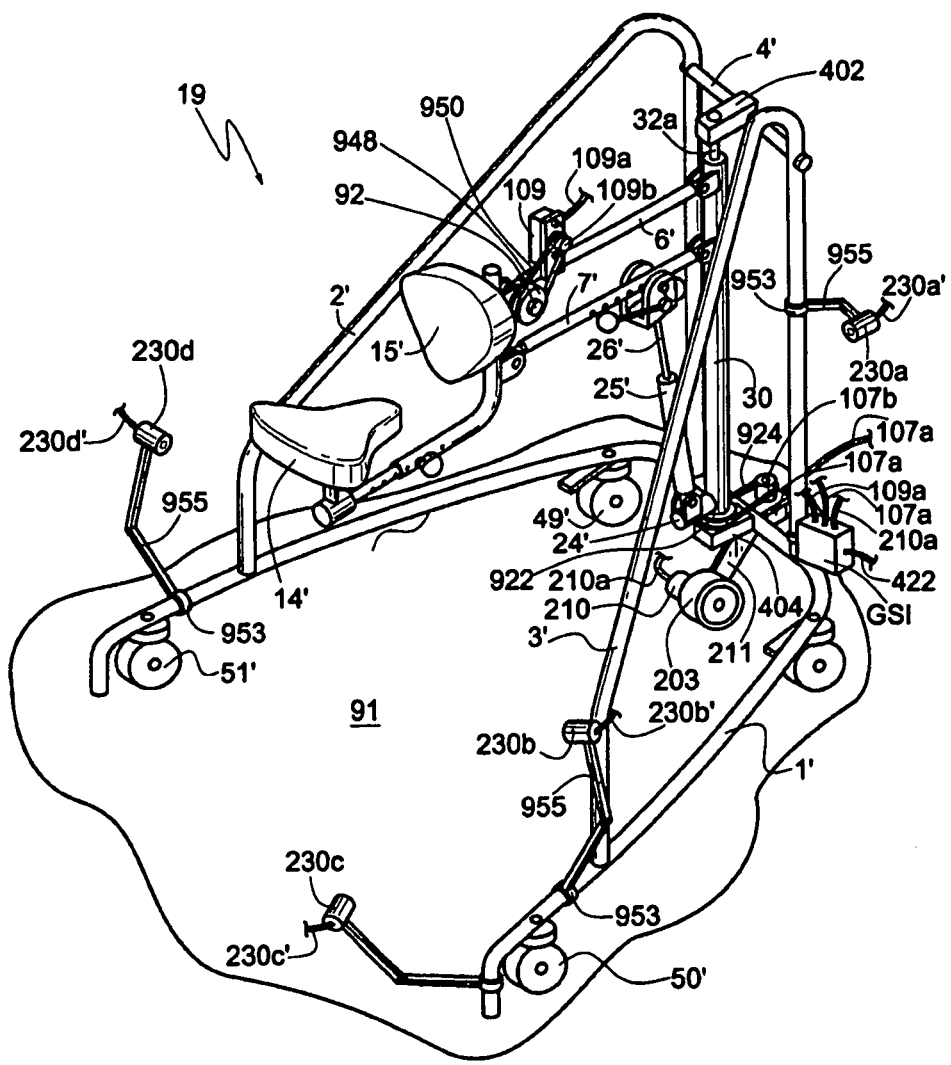
FIG. 19 is a perspective view of another example of a gait analysis system of the present invention used with a body support system having a user-adjustable body weight support during gait training exercise and analysis over a fixed surface.
Figure 20A:
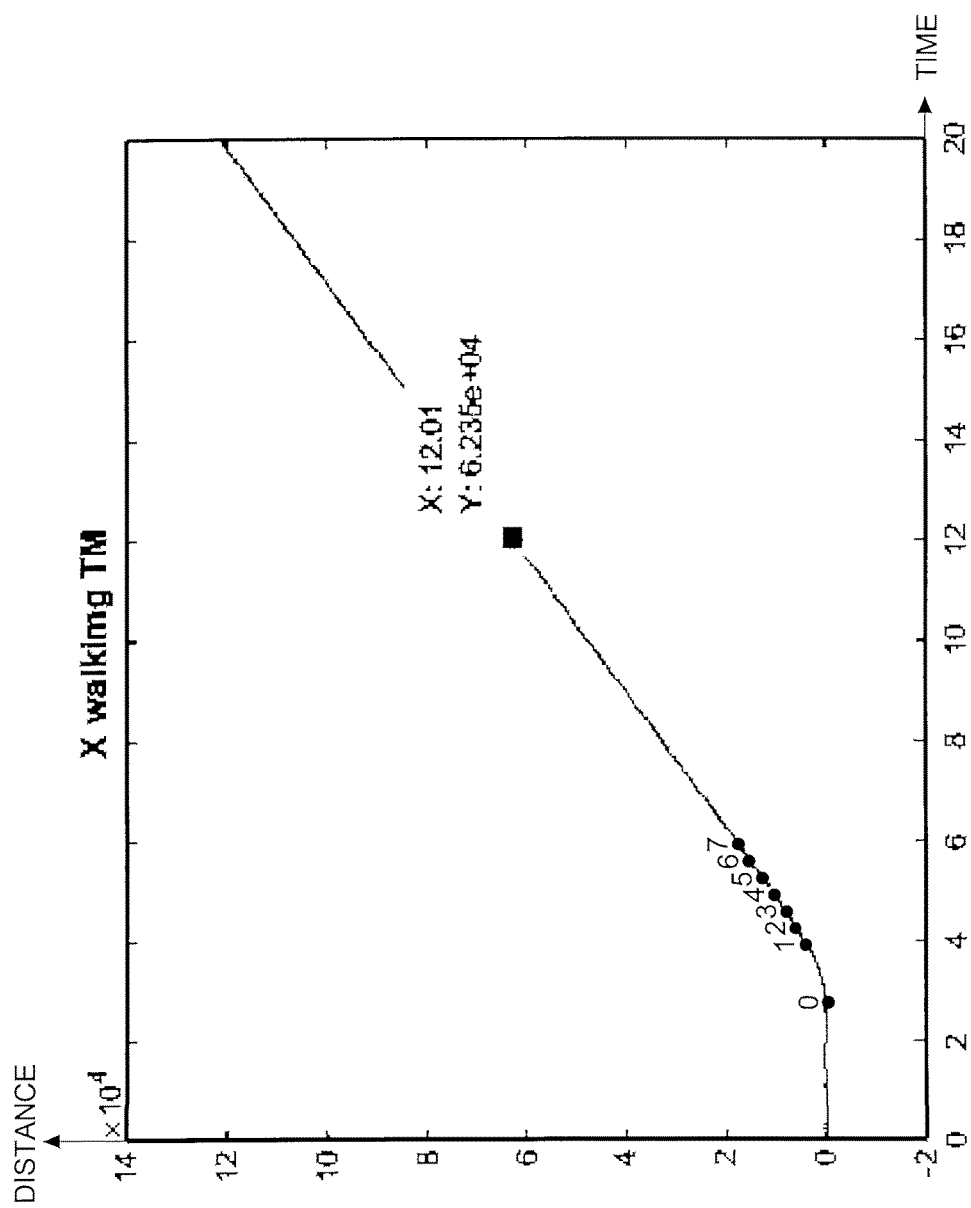
FIG. 20(*a*) through FIG. 20(*e*) illustrate one example of a gait analysis for a gait analysis system of the present invention where a combination of gait measurement graphical data video display windows are provided for the gait analysis time period.
Figure 20B:
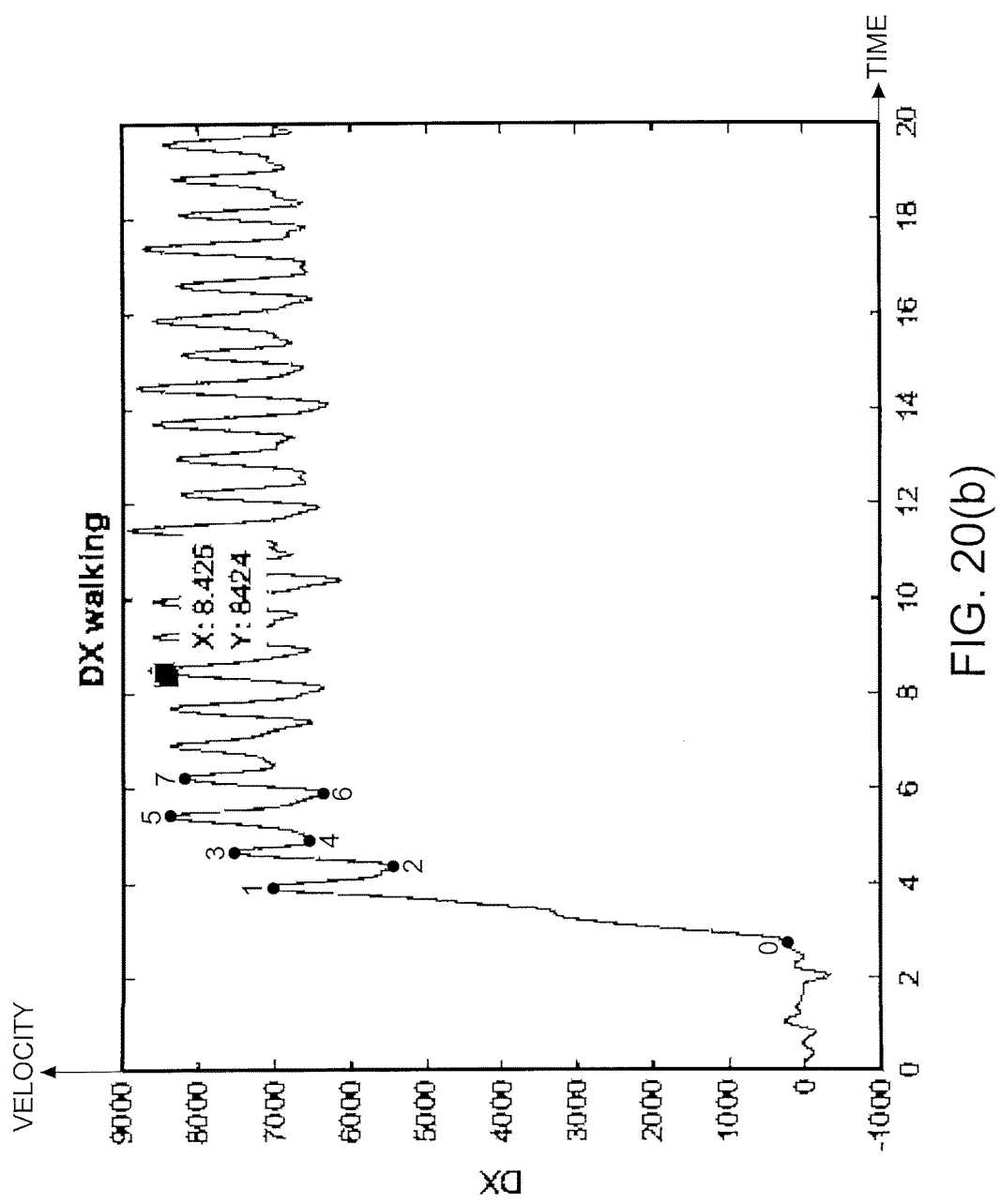
Figure 20C:
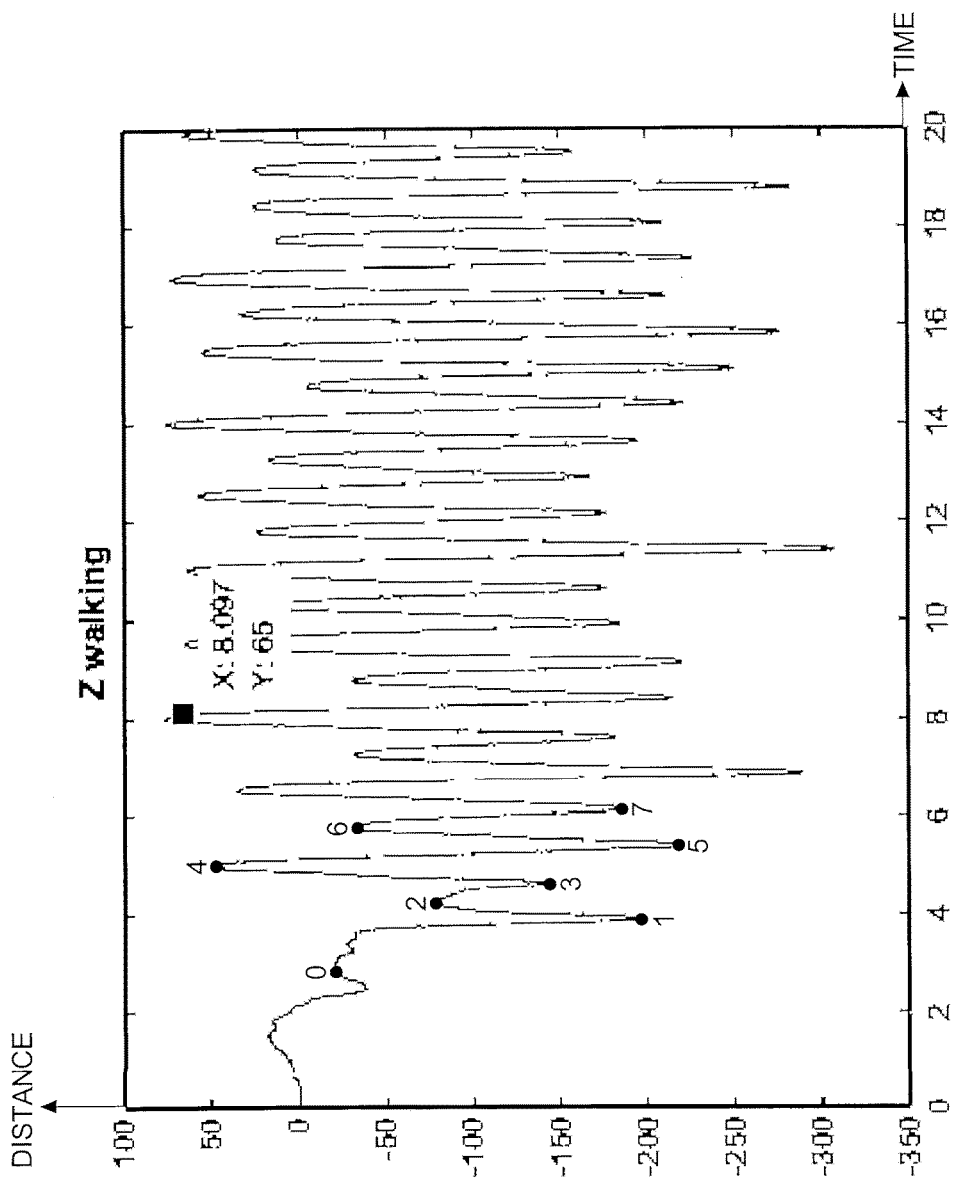
Figure 20D:
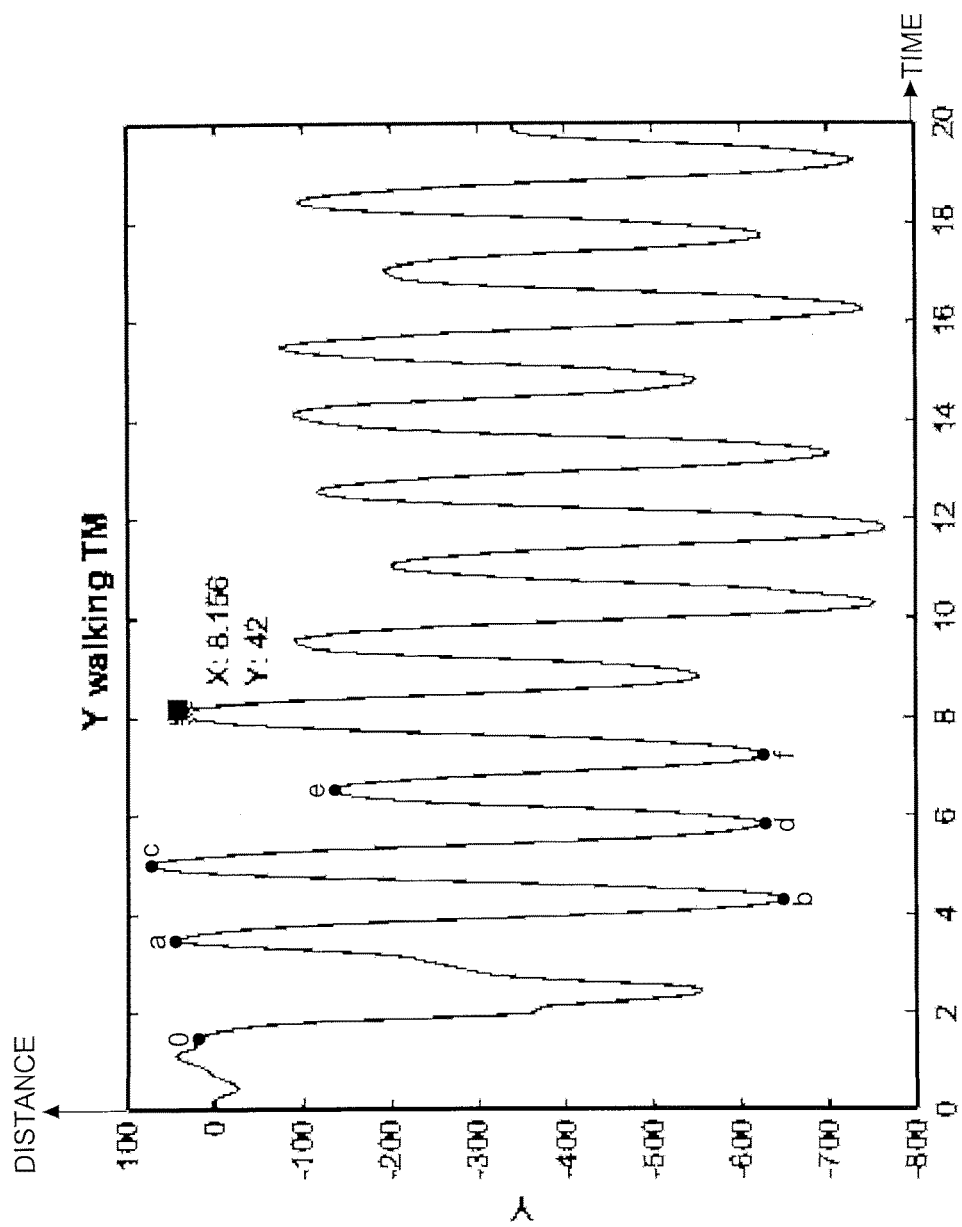
Figure 20E:
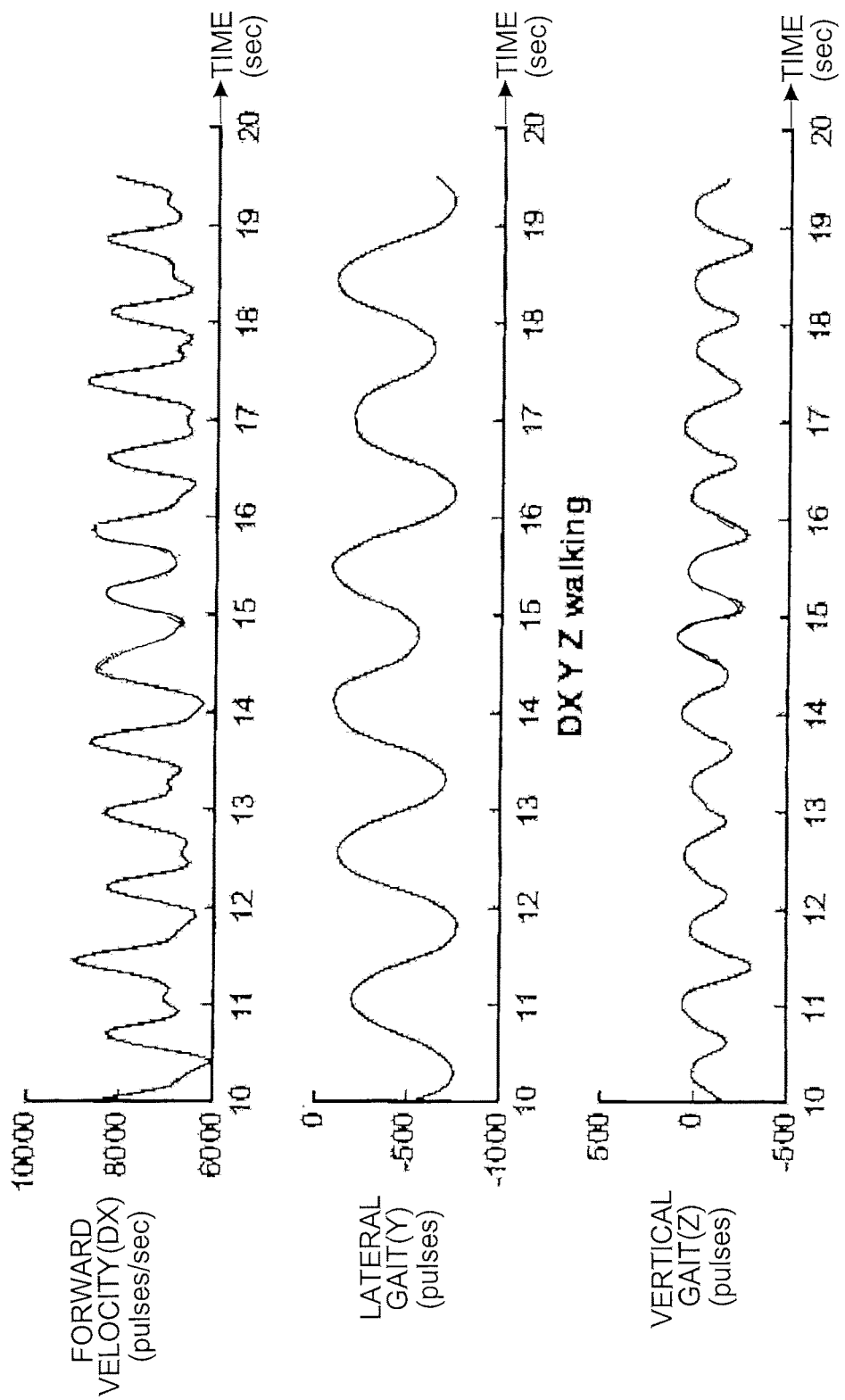

There is shown in FIG. 19 another example 19 of the present invention where a gait analysis system is combined with a body support system having a user-adjustable body weight means that is used on fixed (ground) surface 91. Example 19 is similar to that shown in FIG. 17 except that the body support system in FIG. 19 is modified from that shown in FIG. 17 to provide alternative Y-direction and Z-direction gait measurement sensors. The alternative Y-direction and Z-direction gait measurement sensors are similar to those shown in FIG. 14 and are provided by modifying the body support system 17' shown in FIG. 17. In FIG. 19, sleeve connections 10' and 11' and cross bar 5' are removed between arcuate side members 1' and 2' of the body support system in FIG. 17.

In the example of FIG. 19 rotational shaft 30 is a hollow cylindrical shaft that is pivotally attached to upper standoff bar 402 that is rigidly connected to the horizontal center of cross bar 4' by top pin 32*a* and similarly pivotally attached to lower standoff bar 404 that is rigidly connected to the horizontal center of frame base 1'. The ends of position stabilizing bar 6' and support lever 7' previously connected to the removed sleeve connections 10' and 11' are connected to rotational means 30 in FIG. 19 in similar fashion as position stabilizing arm 42 and support lever 44 are connected to rotational means 30 in FIG. 14. The end of support frame base extension 24' previously connected to the frame base 1' is connected to rotational means 30 in FIG. 19 in similar fashion as rotational shaft offset 30*c* is connected to rotational means 30 in FIG. 14. With these modifications to the body support system in FIG. 17 as shown in FIG. 19 the example 19 of the present invention in FIG. 19 uses a combination of the Y-direction and Z-direction distance measurement sensors shown in FIG. 14 and X-direction distance measurement sensor shown in FIG. 17.

In FIG. 19 forward (X) gait measurement (or directional distance) sensor is provided to measure the distance a user positioned in the body support system shown in FIG. 19 moves in the forward X-direction over fixed surface 91 in a time period. In this example the forward X-direction distance sensor is X-rotary encoder 210 that is suitably fixed to the front of frame base 1'. In this example of the invention X-rotary encoder 210 is attached to the front of frame base 1' via X-support arm 211 that is fixedly attached to frame base 1'. In this example forward X-omniwheel 203 is fixedly attached at one end of X-support arm 211 and is in contact with fixed surface 91 and rotates in the X-direction while allowing movement in other directions along the fixed surface. X-rotary encoder 210 is fixedly attached to one end of the X-support arm and has an X-rotary encoder output shaft connected to the rotational axis of X-omniwheel 203 so that the X-rotary encoder output shaft rotates with omniwheel 203 only in the forward X-direction. X-rotary encoder 210 has a wired output 210*a* connected to the GSI enclosure.

In FIG. 19 a lateral (Y) gait measurement (or directional distance) sensor is provided in this example of the invention to measure the distance that lateral displacement rotational means 30 rotates with the rotational angle being proportional to the lateral gait distance of the user of the body support system. In this example the lateral (Y) direction distance sensor is Y-rotary encoder 107. Y-rotary encoder is suitably fixed to base frame 1'. In this example Y-rotary encoder 107 has Y-encoder cable 107*a* suitably connected to the GSI enclosure. Annular ring 922 is fixed to the bottom end of lateral displacement rotational means 30 and has an annular groove around its outer circumference for fitting of drive belt 924 which belt is also suitably fitted around Y-encoder output shaft 107*b* so that rotation of the lateral displacement rotational means 30 drives rotation of Y-encoder output shaft 107*b* by an angle proportional to the angle of rotation of the lateral displacement rotational means. The angle of rotation of the Y-encoder's output shaft proportionately corresponds to gait distance in the lateral Y-direction.

In FIG. 19 a vertical (Z) gait measurement (or directional distance) sensor is provided to measure the distance that stabilizing arm opposing end of position stabilizing arm 6' rotates as the user moves in the upward or downward direction with the rotational angle being proportional to the vertical gait distance of the user of the body support system. In this example the vertical distance sensor is rotary encoder 109 that is suitably fixed to position stabilizing arm 6'. In this example Z-rotary encoder 109 has Z-encoder cable 109*a* suitably connected to the GSI enclosure. Fastener 92 in this embodiment of the invention is fixed through horizontally aligned holes in "U" shaped position stabilizing arm end while being rotatable around front body support post connector that is inserted in a "U" shaped position stabilizing arm end. Fastener 92 is extended at one end so that Z-direction pulley 948 can be fixed to the extended end as shown in FIG. 19. Belt 950 is fitted in the groove of the pulley and around Z-encoder shaft 109*b* so that rotation of the position stabilizing arm 6' drives rotation of Z-encoder shaft 109*b* by an angle proportional to the angle of rotation of the position stabilizing arm. The angle of rotation of the Z-encoder's output shaft proportionately corresponds to gait distance in the vertical Z-direction.

The gait analysis systems used with a body support system having a user-adjustable body weight means for gait training exercise and analysis on a fixed surface, for example, as shown in FIG. 16, FIG. 17 or FIG. 19, may optionally include floor sensors that may be force platforms or pressure measurement systems where gait is measured by pressure or force sensors and moment transducers where a user in the body support system walks on them over a fixed surface. These floor sensors are generally referred to as non-wearable gait sensors. In some examples of the present invention a pressure sensing array (commonly know as a gait pressure pad) for measuring forces applied thereto when ambulating over the pressure pad is used. Pressure pads are known in the art, for example, as disclosed in U.S. Pat. No. 5,952,585 which is incorporated herein by reference in its entirety. In the examples of the invention including pressure pads the data obtained from the pressure pad can be integrated with the gait analysis data obtained from the body support system for gait training exercise and gait analysis over a fixed surface.

As an alternative to floor systems, the gait analysis system that is used with a body support system for gait training exercise and analysis over a fixed surface, for example, as shown in FIG. 16, FIG. 17 or FIG. 19, may optionally be used with user wearable foot pressure sensors, for example, as disclosed in United States Patent Application Publication No. 2014/0326085 A1 which is incorporated herein by reference in its entirety. The wearable foot pressure sensors may be integrally incorporated into the footwear of a user of a body support system with gait analysis sensors of the present invention, inserted into the footwear, for example as an insertable pressure sensing insole, or otherwise located on a user, such as the bottom foot surfaces of socks worn by a user.

Non-wearable foot pressure pads have an advantage over wearable foot pressure sensors in that the X-Y array of pressure sensors in a pressure pad can be calibrated to a physical position on the fixed surface (X-Y plane) and therefore position calibrated to the user in the body support system as it moves over the pressure pad. With wearable insole pressure pads the physical position over the fixed surface can be calibrated with the output data from the distance encoders.

In general wearable or non-wearable foot pressure pads are referred to herein as a foot pressure level sensor having an array of foot having an array of foot variable pressure level sensors having variable pressure level outputs comprising one of a plurality of gait sensor signals for processing by a gait analysis processor to output to gait analysis personnel a foot variable pressure video image of the user.

In other examples of the present invention the wearable gait sensors comprise separate toe and heel sensors for each foot of a user of the body support and gait analysis system of the present invention where each sensor is a bi-state (switch) sensor. A heel strike sensor changes state when a heel region of the user makes initial contact with ground surface 91 (heel strike) in a gait cycle and stays in that heel strike state until the heel leaves the ground (heel off) in a gait cycle. The toe off sensor changes state when the toe region of the user initially leaves the ground in a gait cycle and stays in that toe off state until the toe region of the user again makes contact with the ground in the gate cycle. The toe and/or heel sensors may be integrally incorporated into the footwear of a user of the body support system or discretely inserted into or onto the footwear, for example, on an insertable sensing insole, or otherwise located on a user, such as the bottom foot surfaces of socks worn by a user. Positioning of the toe and heel sensors in the toe and heel regions when a toe or heel strike sensor changes state can be adjusted for a particular user to insure sensor state change at the appropriate time in the gait cycle. Wired connections 602 and 604 can be connected to the GSI enclosure mounted on the frame of any body support system used with gait analysis sensors of the present invention as shown in FIG. 22 for example 19 in FIG. 19.

In some embodiments of the invention electromyography (EMG) sensors, as known in the art, are attached to the user of a gait analysis system of the present invention while on a body support system to analyze selected muscles associated with a gait analysis and for processing by the gait analysis processor or a dedicated electromyography processor to output electromyography data to the gait analysis personnel as, for example, an electromyography graphical data display.

Figure 21A:
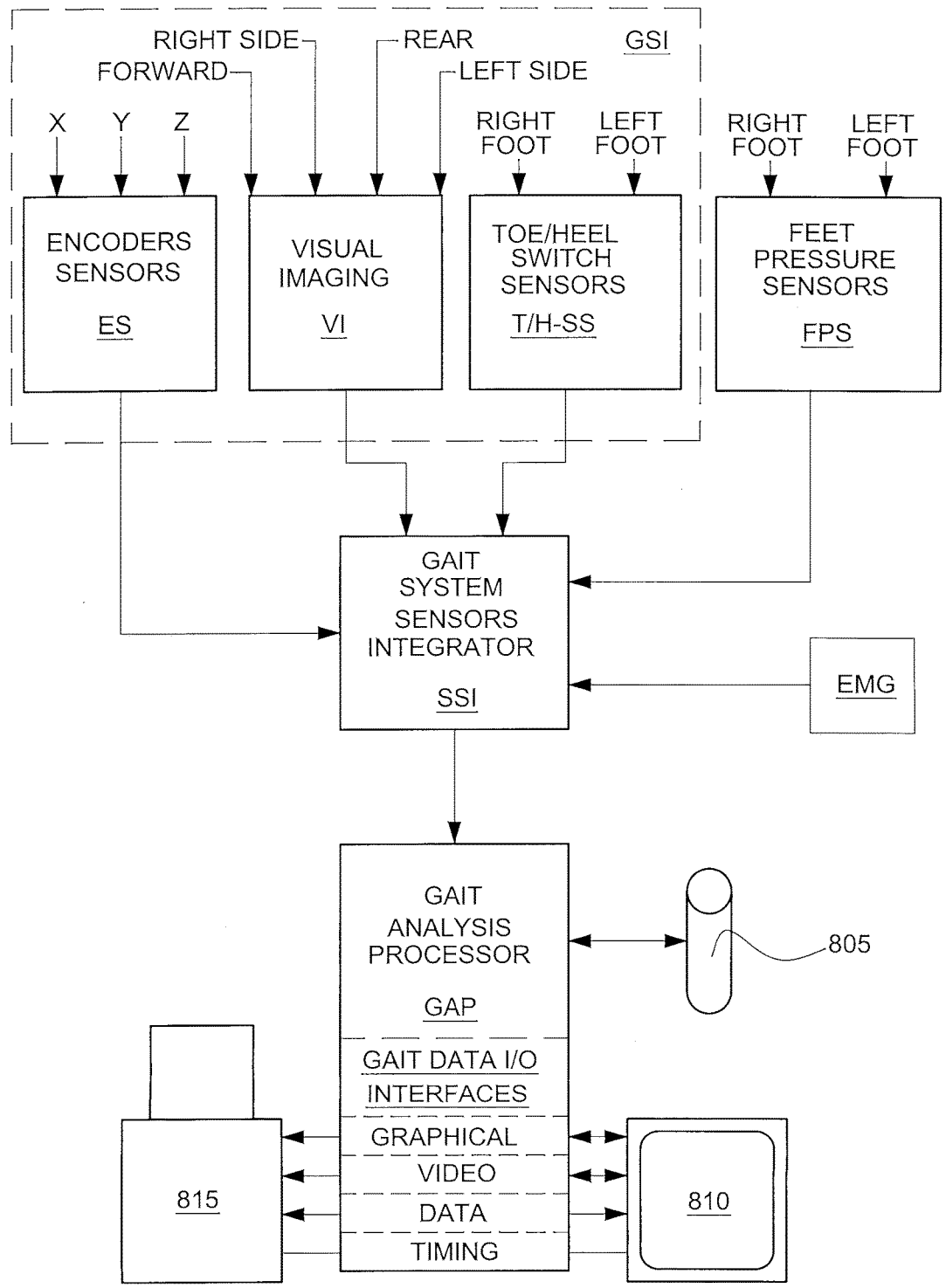
FIG. 21(*a*) is a composite block diagram for various optional gait analysis systems used with the body support systems of the present invention for gait training exercise and analysis over a treadmill or fixed surface.
Figures 21B, 22:
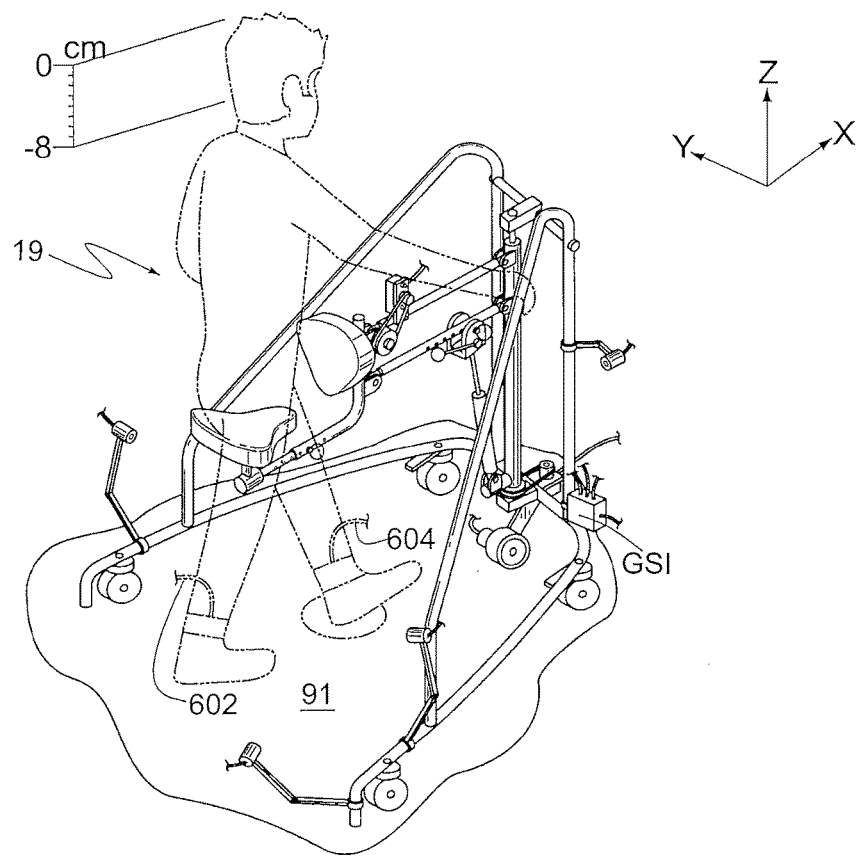
FIG. 22 illustrates one example of measuring the change in the vertical (Z) direction during a gait cycle.

FIG. 21(*a*) includes a composite block diagram of gait sensors that can be used in optional configurations for various gait analysis systems of the present invention that are used with body support systems having a user-adjustable body weight force over a treadmill or fixed surface. X and Z (and optional Y) direction rotary encoders output user data (ES) can be transmitted to the system gait sensors integrator (GSI) that can be a GSI enclosure on a body support system as shown in the figures. If visual sensors are used the user video sensor output signals (VI) from the one or more visual sensors can be transmitted to the GSI enclosure. If non-wearable feet pressure sensors (FPS) are used, the array of feet pressure user data outputs can be provided directly to the gait system sensors integrator (SSI) or indirectly after pre processing with a dedicated FPS processor. If wearable feet pressure sensors, feet pressure user data outputs can be inputted optionally to the GSI enclosure, directly to the SSI or indirectly after processing with a dedicated FPS processor. If toe/heel switch sensors are used in an embodiment of the invention, toe/heel bi-state output data (T/H-SS) from the outputs of the toe/heel switch sensors can be transmitted to the GSI enclosure on the body support system.

In some embodiments of the transition of output sensors data to the GSI may be wired or wireless. Further the GSI may be located remote from the body support system in some examples of the invention.

The SSI inputs the collected output sensors data from the gait sensors used in a particular embodiment of the invention from the GSI to the gait analysis processor GAP which communicates with electronic storage device 805 for storage and/or retrieval of collected gait system data and processing the collected gait system data for outputting the processed data. GAP I/O interfaces include graphical (either to printer 806 or video display 810 that may be a touch input screen or interfaced with another gait analysis technician's means of inputting data into the processor) and video that may be time synchronized with the graphical data to observe one or multiple user video display(s) of the user ambulating on the body support system synchronized with gait graphical data.

At least the ES, VI and T/H-SS are inputted to the GSI that is an enclosure mounted on the body support system in the preferred embodiments of the invention shown in the figures. In other embodiments of the invention the GSI may be remotely located from the body support system. If remotely located, data transmission from the body support system gait sensors can be provided either by a wired or wireless communications system with suitable data protocol. As shown in the drawings GSI wired output 422 transmits the sensors outputs to the SSI. In some embodiments of the invention the GSI and SSI may be combined into a single device for transmitting of sensor data directly or indirectly via interface devices to the GAP The table in FIG. 21(*b*) illustrates preferred, but not limiting, sample alternative gait analysis systems used with the body support systems of the present invention. The sample alternative analysis systems progress from 1 to 5 in complexity of the gait analysis system that may be utilized as follows.

Alternative analysis system 1 utilizes the output data from the encoder sensors to evaluate movement of the user's center of mass in a gait cycle while visually viewing the user's lower body movement during the gait cycle to provide a low cost system of the present invention, for example, in a clinical environment, such as rehabilitation treatment of an ankle injury.

Alternative analysis system 2 builds on system 1 by providing data on times of heel strike and toe off in a gait cycle. Knowing the times in the gait cycles when these events occur can be used to determine gait cycle parameters. For example, time of a heel strike in a gait cycle can be used to calculate impact velocity.

Alternative analysis system 3 builds on system 2 with the user video sensor output signal being inputted to an image processing system to output one or more gait diagnostic parameters such as knee angles or ankle positions relative to the user's center of mass as determined by the encoder sensors.

Alternative analysis system 4 builds on system 3 with non-wearable or wearable feet pressure data is inputted optionally with toe off/heel strike sensing data.

Alternative analysis system 5 builds on system 4 with electromyography body sensors and data analysis.

Graphs in FIG. 20(*a*) through FIG. 20(*e*) illustrate one example of a graphical output from a gait analysis system of the present invention, for example, by execution of a gait analysis software by processor GAP in FIG. 21(*a*) with output to video display 810 or printer 815.

FIG. 20(*a*) (graph-1) is one example of a graphical output from a gait analysis system of the present invention where the graph X-axis represents time and the graph Y-axis represents the distance (in operator selectable units such as meters or feet) of user forward walking in the X-direction while in a body support system for gait exercise over a fixed surface. At graph-1 point 0 walking starts for a period of 20 seconds, which can represent in this example FIG. 16 rotary encoder 210 output of 120,000 pulses. User velocity (V) can be calculated by system software in In FIG. 20(*b*) (graph-2) the graph X-axis represents time and the graph Y-axis represents forward walking velocity (v) or speed of the user in the body support system as an output graphical display of the gait analysis system. Walking velocity in FIG. 20(*b*) can be determined by gait analysis system software executed by gait analysis processor (GAP) in FIG. 21 as the mathematical first derivative of distance (in graph-1).

Since human walking is bipedal, walking velocity varies every time the user in the body support system pushes forward with a leg in a gait cycle. For example in FIG. 20(*b*) from point 0 to point 1, the user accelerates approximately 7,000 rotary encoder 210 output pulses per second, and from point 1 to 2 the user decelerates approximately 7,000 pulse per second when a user's leg is swinging forward. Between graph-2 points 2 and 3, acceleration occurs again (that is, the user pushing forward in the body support system) with the above-described acceleration/deceleration cycle repeating as the user moves forward by alternative use of right and left legs. Graph-2 points 1, 3, 5 and 7 are where the user is at a maximum speed, and graph-2 points 2, 4, 6 and 8 are where the user is at a minimum speed. By determining the time between graph-2 points 1 to 3; 3 to 5; and 5 to 7 with the gait analysis system software, processor GAP in FIG. 21(*a*) can determine the time period of each user step, and from the data in FIG. 20(*a*), the user step sizes overall from the data in FIG. 20(*a*) and FIG. 20(*b*), processor GAP can determine: the number of steps; an average step time; and a variability (for example, as a standard deviation) step size. With determination of left leg and right leg average step size synchronized with time, processor GAP can analyze gait symmetry between the user's left and right legs with the gait analysis system software and output the data to a suitable device such as video display 810 and/or printer 815 in FIG. 21(*a*).

In FIG. 20(*c*) (graph-3) the user's vertical gait (Z-axis) movement, which is represented by graph-3 Y-axis) while moving forward in the body support system is determined from FIG. 16 rotary encoder 220 output pulses per second data that is inputted to the gait analysis system. At graph-3 point 0, user walking starts to rise then falls at graph-3 point 1. Graph-3 points 1, 3, 5 and 7 are at minimum vertical speed and graph-3 points 2, 4 and 6 are at maximum speed. User vertical step size can be determined by processor GAP in a manner similar to that for determining forward step size from the data displayed in FIG. 20(*b*), and processor GAP can analyze the coordination between forward velocity and vertical user movement with the gait system software to quantify efficiency of the user's kinetic energy and potential energy in a gait cycle when using the body support system. The data can be output to a suitable device such as video display 810 and/or printer 815 in FIG. 21(*a*).

In FIG. 20(*d*) (graph-4) the user's lateral gait (Y-axis) movement, which is represented by graph-4 Y-axis, while moving forward in the body support system is determined from FIG. 16 rotary encoder 215 output pulses per second data that is inputted into the gait analysis system. Graph-4 points a, b, c, d and e illustrate the lateral movement from left leg to right leg or vice versa. At graph-4 points a, c and e, the user is on either the left or right leg while at points b, d and f, the user is on the opposite right or left leg respectively. As shown in FIG. 20(*d*) the lateral gait movement frequency is one-half of the vertical gait movement frequency and the forward gait velocity since every complete lateral gait movement cycle comprises two steps. Processor GAP can determine the average lateral gait movement cycle time; and a variability (as a standard deviation) in the lateral gait movement cycle size and output the data to a suitable device such as video display 810 and/or printer 815 in FIG. 21(*a*).

In FIG. 20(*e*) (graph-5) by execution of the gait analysis system software, processor GAP can dynamically determine and output the position of the user's center of mass while walking forward in the body support system from the inputted forward velocity time-synchronized with the vertical and lateral gait movements as displayed, for example, in graph-5 where the three curves (from top to bottom) illustrate time synchronized; forward (X) user velocity (that is, the mathematical derivative (DX) of forward gait distance; lateral (Y) user gait distance measured in encoder pulses, which can be converted to any linear dimension depending upon a particular converter; and vertical (Z) user gait distance also measured in encoder pulses in this example.

FIG. 23(a) through FIG. 23(d) illustrate another example of the gait analysis system of the present invention where encoder sensors, video imaging sensors and bi-state toe/heel sensors are used with the body support system shown in FIG. 19. Each of the four figures represents a snapshot of one example of a continuous video display in the gait analysis system as the user goes through a gait cycle. With reference to FIG. 1, the sequence of heel strikes and toe strikes progress from right heel strike (RHS); left toe off (LTO); left heel strike (LHS); to right toe off (RTO). The video display snapshots in this example include six graphic display windows arranged vertically from top to bottom as follows.

Video window 502 displays forward velocity (DX) measured from 20 to 100 centimeters per second (cm/sec) along the y-axis.

Video window 504 displays vertical gait position (Z) measured from −8 to 0 cm along the y-axis where 0 cm is a user body reference point when the user body vertical reference point is at its highest vertical distance from fixed ground and minus 8 when the user body vertical point is at its lowest vertical distance from fixed ground 91. A user's body is at its highest vertical distance when the user is standing stationary in the full upright position of a body support system of the present invention as illustrated, for example, in FIG. 5. The user body vertical reference point can be, for example, the top of the user's head as illustrated in FIG. 5 or FIG. 22.

Video window 506 displays right heel strike sensor state which is a gait cycle bi-state value of the right heel sensor that is at state 1 from the time that the right heel makes contact with the ground (heel strike) until the right heel leaves the ground (heel off) during a gait cycle and at state 0 for the remainder of a gait cycle.

Video window 508 displays right toe off sensor state which is a gait cycle bi-state value of the right toe sensor that is at state 0 from the time that the right toe leaves the ground (toe off) until the right toe makes contact with the ground during a gait cycle and at state 1 for the remainder of a gait cycle.

Video window 510 displays left heel strike sensor state which is a gait cycle bi-state value of the left heel sensor that is at state 1 from the time that the left heel makes contact with the ground (heel strike) until the left heel leaves the ground (heel off) during a gait cycle and at state 0 for the remainder of a gait cycle.

Video window 510 displays left toe off sensor state which is a gait cycle bi-state value of the left toe sensor that is at state 0 from the time that the left toe leaves the ground (toe off) until the left toe makes contact with the ground during a gait cycle and at state 1 for the remainder of a gait cycle.

In some examples of the invention the 0 and 1 states may be selectively reversed.

Video window 514 represents one or more optional display windows for other gait graphical data such as lateral gait position (Y) or electromyography data.

Video display window 516 is positioned to the right of the six graphic display windows in this example of the invention. In the figures video display 516 is represented by the entire user body and body support system. However actual video display window content is the lower body (hips and legs) of the user body as captured by one or more of the video cameras mounted on the body support system relative to movement on fixed ground 91.

The video display frames, typically at a low frame rate (for example 100 frames per second) can be time synchronized with the encoders' high data rate (typically 1,000 pulses per sec) by the gait analysis processor.

Different grouping of video display windows may be used in other example of the invention, for example, if a feet pressure level sensors pad is used, foot pressure imprints (color coded or shades of gray coded for pressure value) may be displayed in optional video display window 518 and synchronized with the content of video display window 516 and/or graphic display windows 502 to 512)

The outputs of heel and toe sensors are fed from the user by cables 602 and 604 to the GSI on the body support system in the present example as illustrated in FIG. 22.

Figure 23A:
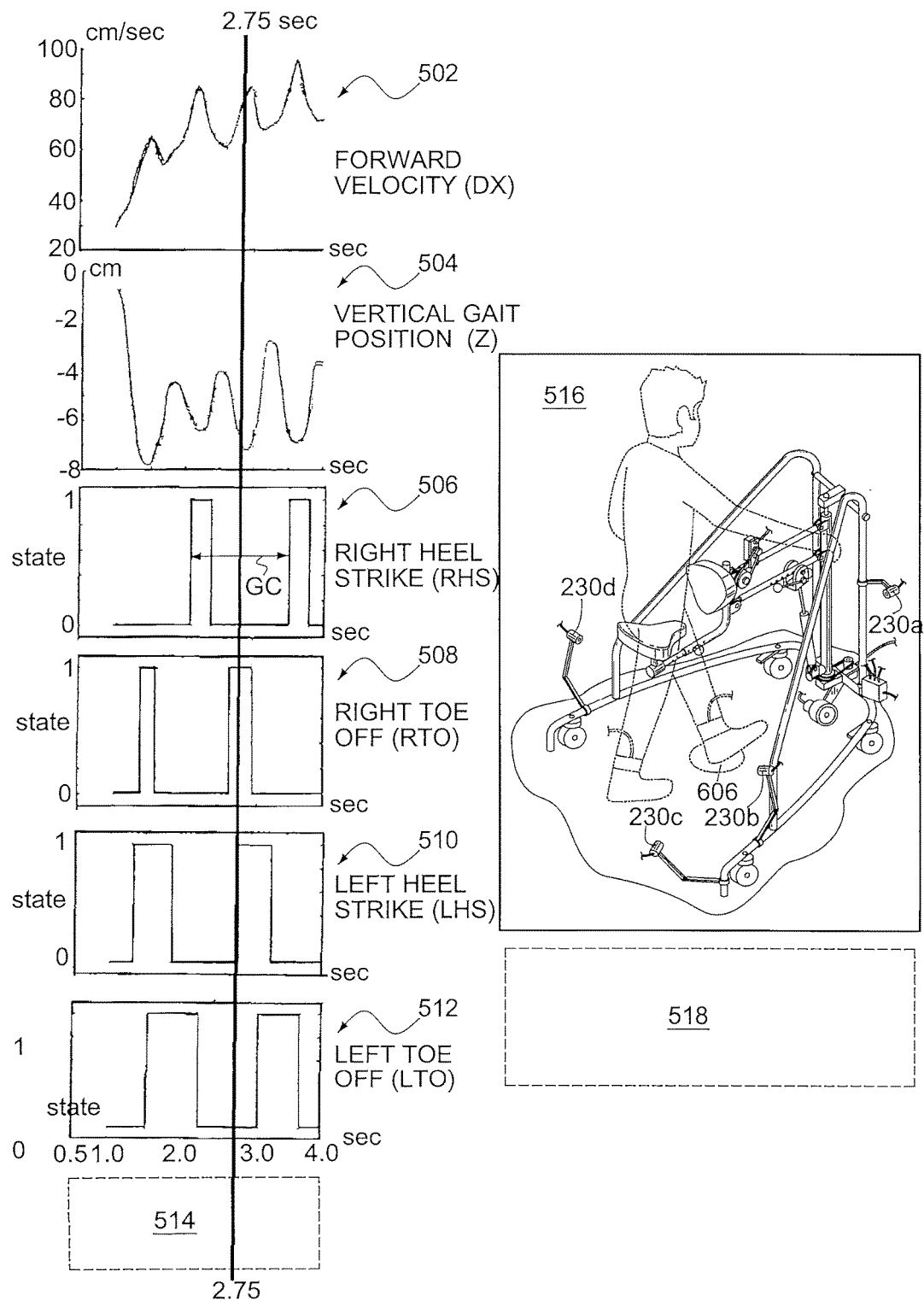
FIG. 23(*a*) through FIG. 23(*d*) illustrate one example of gait analysis output video displays for a gait analysis system of the present invention where a combination of gait measurement graphical data video display windows and a user gait-focused video display window are provided for the gait analysis time period.

As indicated by the circular region 606 on fixed surface 91 in video display window 516 in FIG. 23(a) the gait cycle video snapshot is taken at left heel strike at the indicated 2.75 sec of gait analysis.

Figure 23B:
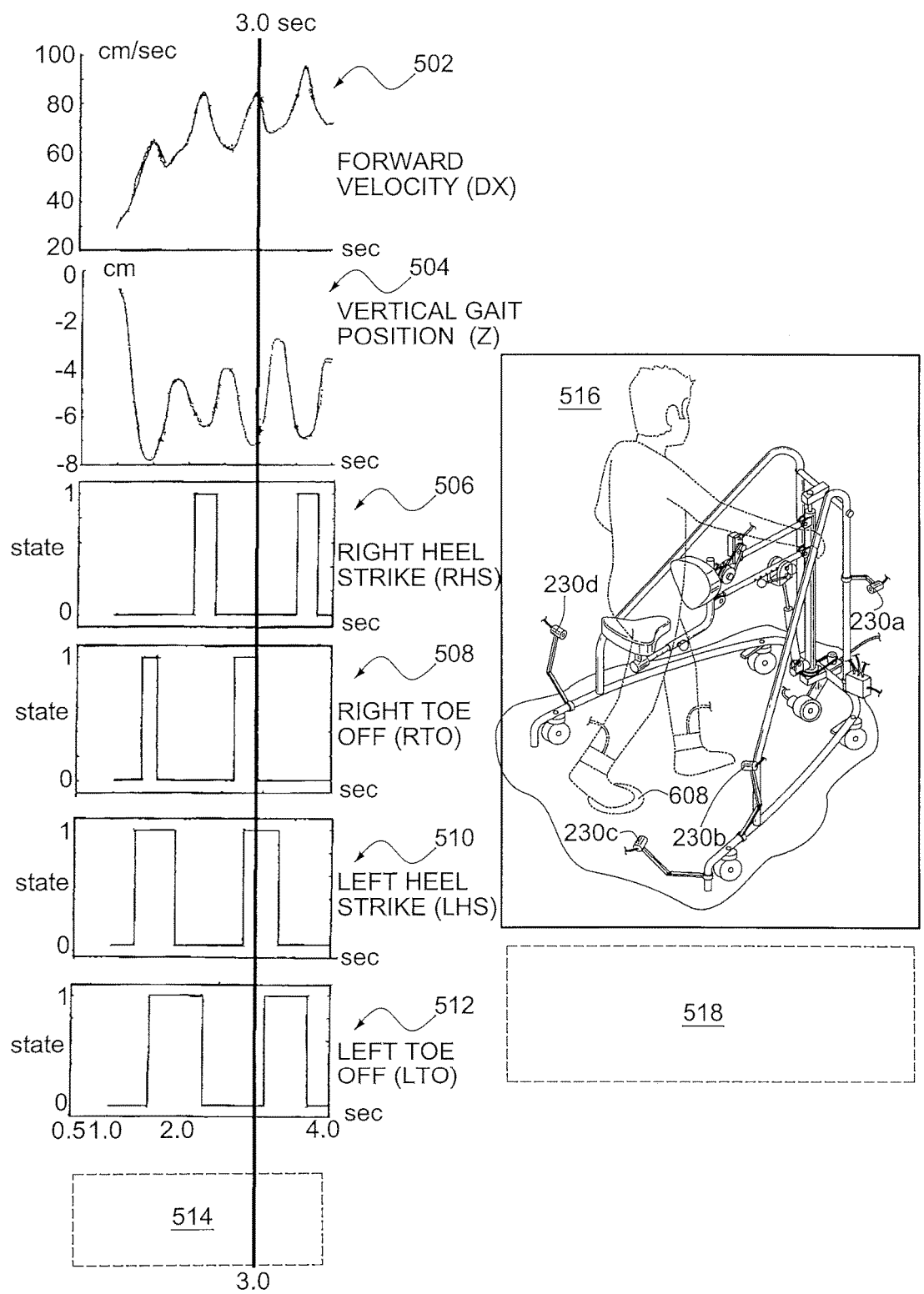

As indicated by the circular region 608 on fixed surface 91 in video display window 516 in FIG. 23(b) the gait cycle video snapshot is taken at right toe off at the indicated 3.0 sec of gait analysis.

Figure 23C:
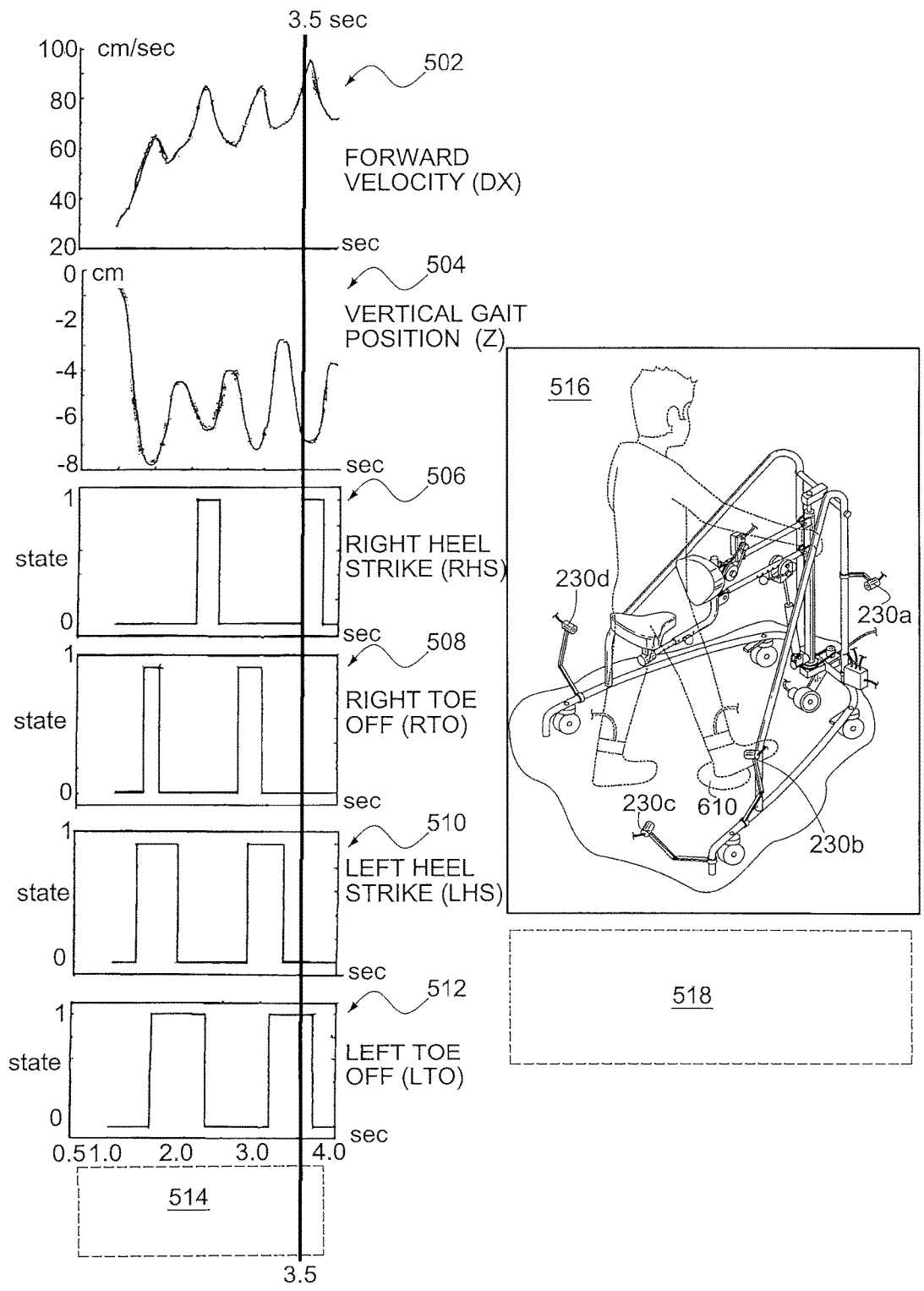

As indicated by the circular region 610 on fixed surface 91 in video display window 516 in FIG. 23(c) the gait cycle video snapshot is taken at right heel strike at the indicated 3.5 sec of gait analysis.

Figure 23D:
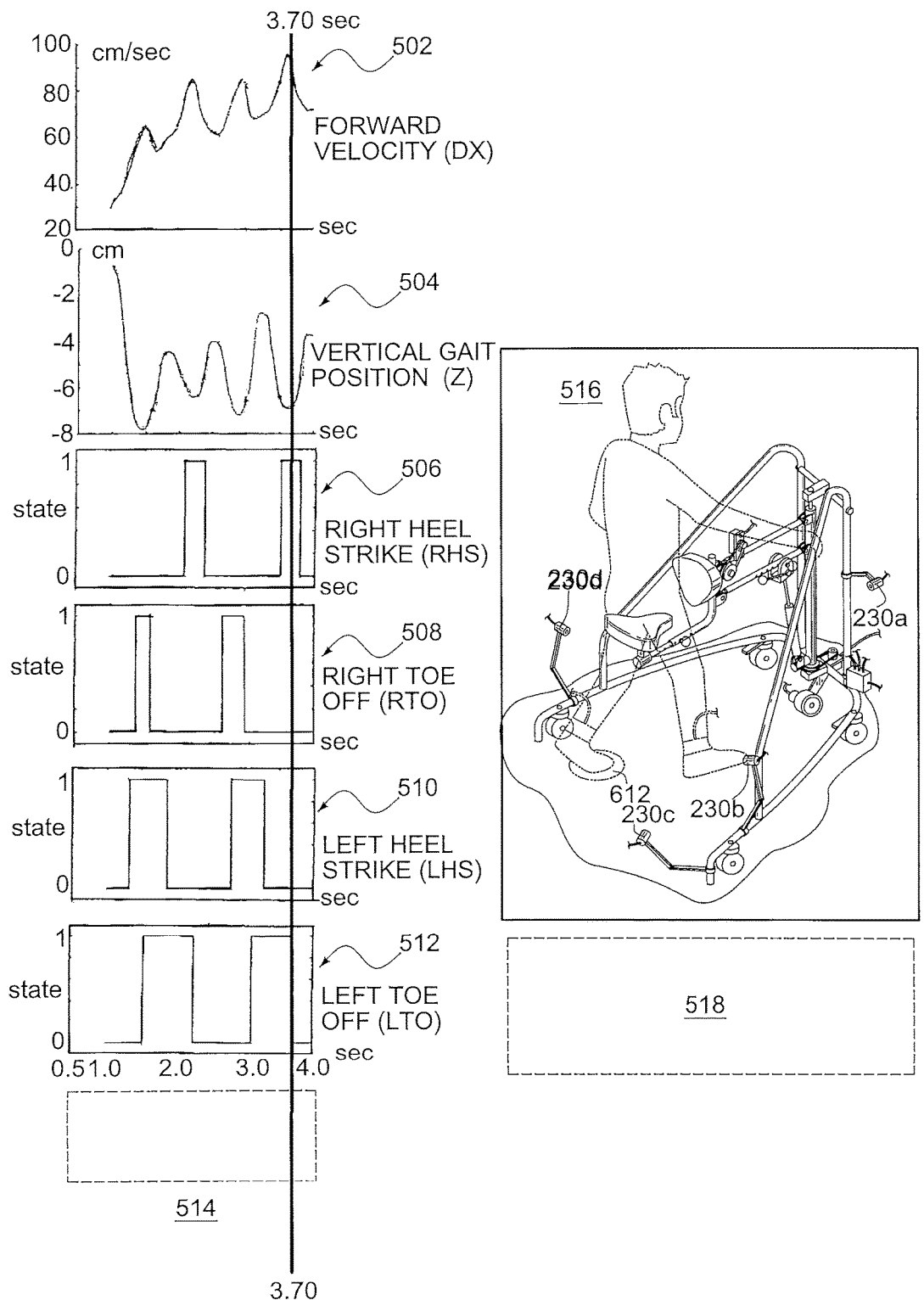

As indicated by the circular region 612 on fixed surface 91 in video display window 516 in FIG. 23(d) the gait cycle video snapshot is taken at right toe off at the indicated 3.7 sec of gait analysis.

Each snapshot with multiple graphs and video display provide simultaneous gait graphical data with visual display of the user's lower body on the body support system.

Reference throughout this specification to "one example or embodiment," "an example or embodiment," "one or more examples or embodiments," or "different examples or embodiments," for example, means that a particular feature may be included in the practice of the invention. In the description various features are sometimes grouped together in a single example, embodiment, figure, or description thereof for the purpose of streamlining the disclosure and aiding in the understanding of various inventive aspects.

The present invention has been described in terms of preferred examples and embodiments. Equivalents, alternatives, and modifications, aside from those expressly stated, are possible and within the scope of the invention. Those skilled in the art, having the benefit of the teachings of this specification, may make modifications thereto without departing from the scope of the invention.

The invention claimed is:

1. A gait analysis system for a body support system with provisions for a user self-adjustment of a user's body weight force during ambulation when a user is on the body support system, the gait analysis system comprising:
   a gait measurement system connected to the body support system, the gait measurement system comprising:
   a forward gait measurement sensor;
   a vertical gait measurement sensor; and
   at least one visual sensor;
   a system gait sensors integrator for receiving a plurality of gait sensor signals, the plurality of gait sensor signals comprising at least:
   a forward gait measurement sensor output signal from the forward gait measurement sensor comprising a forward rotary encoder, the forward rotary encoder having a forward rotary encoder output shaft, the forward rotary encoder output shaft connected to a wheel-driven axle of a forward wheel making contact with a treadmill surface that rotates in a forward direction with user ambulation on the body support system over the treadmill surface whereby a forward rotary encoder output signal comprises the forward gait measurement sensor output signal and provides a real time forward user movement data simulated by a forward movement of the treadmill surface making contact with the treadmill surface;

a vertical gait measurement sensor output signal from the vertical gait measurement sensor comprising a vertical rotary encoder, the vertical rotary encoder having a vertical rotary encoder output shaft, the vertical rotary encoder mounted on the body support system, the vertical rotary encoder output shaft connected to a vertical rotational element of the body support system that rotates in a vertical direction with user ambulation on the body support system over the treadmill surface whereby a vertical rotary encoder output signal comprises the vertical gait measurement sensor output signal and provides a real time vertical user movement data proportional to the rotation of the vertical rotational element; and a user video sensor output signal from the at least one visual sensor.

2. The gait analysis system of claim 1 wherein the at least one visual sensor comprises a forward user imaging camera; a rear user imaging camera; a left user imaging camera and a right user imaging camera.

3. The gait analysis system of claim 1 further comprising:
a gait measurement system sensors integrator for receiving the plurality of gait sensor signals from the system gait sensors integrator;
a gait analysis processor for processing the plurality of gait sensor signals; and
a gait data input/output system for outputting a processed plurality of gait sensor signals to one or more output devices for a gait analysis personnel and for inputting commands from the gait analysis personnel to the gait analysis processor.

4. The gait analysis system of claim 1 wherein the plurality of gait sensor signals further comprises a lateral gait measurement sensor having a lateral gait lateral gait measurement sensor output signal from a lateral gait measurement sensor supplied to the system gait sensors integrator.

5. The gait analysis system of claim 4 wherein a lateral rotary encoder comprises the lateral gait measurement sensor, the lateral rotary encoder having a lateral rotary encoder output shaft, the lateral rotary encoder mounted on the body support system, the lateral rotary encoder output shaft connected to a lateral rotational element of the body support system that rotates in a lateral direction with user ambulation on the body support system over the treadmill surface whereby a lateral rotary encoder output signal comprises the lateral gait measurement sensor output signal provides a real time lateral user movement data proportional to the rotation of the lateral rotational element.

6. The gait analysis system of claim 4 wherein the body support system comprises a treadmill body support system comprising:
a stationary support frame, the forward gait measurement sensor attached to a wheel rotating on the treadmill surface and connect to the stationary support frame and the at least one visual sensor connected to the stationary support frame;
a lateral displacement rotational means vertically oriented and rotationally connected about a vertical axis to the stationary support frame, the lateral gait measurement sensor rotationally configured to the lateral displacement rotational means;
a support lever extending between the lateral displacement rotational means and a front body support post, the support lever connected rotationally at a first support lever end to the front body support post and connected rotationally at a second support lever end to the lateral displacement rotational means;
a front body support mounted on the front body support post by a swivel joint so that the front body support is configured to be tilted and adjustably positioned along the front body support post upward or downward, the front body support having a front planar surface;
a seat having a front seat end and a back seat end for supporting the user, the seat mounted on a seat support extension connected to the front body support post and wherein the front seat end is positioned in a direction facing the front body support and the lateral displacement rotational means so that the seat positions the user to face the lateral displacement rotational means to enable the user's body freedom of a lateral gait movement when the stationary support frame is positioned over the treadmill surface and wherein the seat is configured to be adjustably positioned along the seat support extension closer toward or further away from the front body support and wherein the seat is adjustably tilted downward so that the user supported by the seat will be wedged between the seat and the front body support with the user's abdominal region in contact with the front body support;
a position stabilizing arm positioned at an elevation higher than the support lever and parallel to the support lever, the position stabilizing arm extending between the front body support post and the lateral displacement rotational means and being rotationally connected at a first position stabilizing arm end to the front body support post and rotationally connected at a second position stabilizing arm end to the lateral displacement rotational means so that the seat and the front body support are maintained at a constant angle with respect to the treadmill surface as the position stabilizing arm and the support lever move rotationally about the lateral displacement rotational means and the front body support post for the lateral gait movement of the user, the vertical gait measurement sensor rotationally connected to the position stabilizing arm;
an adjustable body weight support spring means rotationally connected to the lateral displacement rotational means for applying an adjustable full or partial weight-bearing supporting force to the support lever so that the seat, the front body support and the user wedged between the seat and the front body support is configured to move up or down and laterally responsive to a variable body force supplied by the user as the user walks, stands or sits over the treadmill surface in the treadmill body support system; and
a control lever mounted on the adjustable body weight support spring means so that upon movement of the control lever an off-center circular disk is turned to a static mode position which releases a gas control pin to limit the movement of a pressurized gas within the adjustable body weight support spring means so that the movement of the seat and the front body support is configured to be locked at variable fixed elevations including a treadmill body support sitting height position to allow the user to enter or exit the treadmill body support system from a wheelchair sitting position and hold the seat, the front body support and the user in a continuous treadmill body support sitting position without the application of the user's body weight force or an external force and so that upon further movement of the control lever the off-center circular disk is turned to a dynamic mode position to activate the gas control pin to release the movement of the pressurized gas within the adjustable body weight support spring means so that the seat, the front body support and the user are not restrained to the treadmill body support sitting height position or a treadmill body support fixed elevational position and is configured to move to a treadmill body support standing or a treadmill body support walking position on the treadmill surface with the user supported by the adjustable full or partial weight-bearing supporting force applied by the adjustable body weight support spring means to allow the user's body freedom of a vertical gait movement.

7. The gait analysis system of claim 1 further comprising a heel strike bi-state sensor and a toe off bi-state sensor for each foot of the user, the heel strike bi-state sensor activated by the user to a first heel bi-state signal output during a heel strike time period of the heel strike of the treadmill surface to a heel off of the treadmill surface and a second heel bi-state signal output during a heel off time period when the heel is not in contact with the treadmill surface during a gait cycle; the toe off bi-state sensor activated by the user to a first toe bi-state signal output during a toe off time period when the toe leaves the treadmill surface to when the toe makes contact with the treadmill surface during the gait cycle and a second toe bi-state signal output during a toe contact period when the toe is in contact with the treadmill surface, the first and second heel bi-state signal output signals and the first and second toe bi-state signal outputs signals each comprising one of the plurality of gait sensor signals.

8. The gait analysis system of claim 7 further comprising a gait parameter video analysis processor for processing the user video sensor output signal, the gait parameter video analysis processor having one or more processed gait parameter outputs provided to a gait analysis personnel.

9. The gait analysis system of claim 1 further comprising:
a foot pressure level sensor having an array of foot variable pressure level sensors having variable pressure level outputs comprising one the plurality of gait sensor signals for processing by the gait analysis processor to a foot variable pressure level data displayed to a gait analysis personnel as a foot variable pressure video image of the user; and
the one or more processed gait parameter outputs comprising a gait parameter video image of the user.

10. The gait analysis system of claim 9 wherein the plurality of gait sensor signals for processing by the gait analysis processor comprises one or more electromyography gait sensor signals provided from one or more user-attached electromyography sensors for processing by the gait analysis processor to an electromyography signal data displayed to the gait analysis personnel as an electromyography graphical data display.

11. A gait analysis system for a body support system with provisions for a user self-adjustment of a user's body weight force during ambulation when a user is on the body support system, the gait analysis system comprising:
a gait measurement system connected to the body support system, the gait measurement system comprising:
a forward gait measurement sensor;
a vertical gait measurement sensor; and
at least one visual sensor;
a system gait sensors integrator for receiving a plurality of gait sensor signals, the plurality of gait sensor signals comprising at least:
a forward gait measurement sensor output signal from the forward gait measurement sensor comprising a forward rotary encoder, the forward rotary encoder having a forward rotary encoder output shaft, the forward rotary encoder output shaft connected to a wheel-driven axle of a forward omniwheel making contact with a fixed surface, the forward omniwheel rotating in a forward direction with user ambulation on the body support system over the fixed surface whereby a forward rotary encoder output signal comprises the forward gait measurement sensor output signal provides a real time forward user movement data;
a vertical gait measurement sensor output signal from the vertical gait measurement sensor comprising a vertical rotary encoder, the vertical rotary encoder having a vertical rotary encoder output shaft, the vertical rotary encoder mounted on the body support system, the vertical rotary encoder output shaft connected to a vertical rotational element of the body support system that rotates in a vertical direction with user ambulation on the body support system over the fixed surface whereby a vertical rotary encoder output signal comprises the vertical gait measurement sensor output signal and provides a real time vertical user movement data proportional to the rotation of the vertical rotational element; and
a user video sensor output signal from the at least one visual sensor.

12. The gait analysis system of claim 11 wherein the at least one visual sensor comprises a forward user imaging camera; a rear user imaging camera; a left user imaging camera and a right user imaging camera.

13. The gait analysis system of claim 11 further comprising:
a gait measurement system sensors integrator for receiving the plurality of gait sensor signals from the system gait sensors integrator;
a gait analysis processor for processing the plurality of gait sensor signals; and
a gait data input/output system for outputting a processed plurality of gait sensor signals to one or more output devices for a gait analysis personnel and for inputting commands from the gait analysis personnel to the gait analysis processor.

14. The gait analysis system of claim 11 wherein the plurality of gait sensor signals further comprises a lateral gait measurement sensor having a lateral gait lateral gait measurement sensor output signal from a lateral gait measurement sensor supplied to the system gait sensors integrator.

15. The gait analysis system of claim 14 wherein the body support system comprises:
a support frame, the forward gait measurement sensor and the at least one visual sensor connected to the support frame;
a roller means mounted on the support frame for contacting the fixed surface and rolling the frame;
a support lever extending between the support frame and a front body support post and connected rotationally at one end to the post and connected rotationally at the other end to the support frame;

a front body support mounted on the front body support post by a swivel joint so that the front body support can be tilted and can be adjustably positioned along the front body support post up or down, the front body support having a front planar surface;

a seat having a front end and a back end for supporting the user, the seat mounted on a seat support extension connected to the front body support post and wherein the front of the seat is positioned in a direction facing the front body support and the support frame so that the seat positions the user to face the body to enable the user's body to push the body support system in front of the user and wherein the seat can be adjustably positioned along the seat support extension closer toward or further away from the front body support and wherein the seat is adjustably tilted downward so that the user supported by the seat will be wedged between the seat and front body support with the user's abdominal region in contact with the front body support;

a position stabilizing arm positioned at an elevation higher than the support lever and parallel to the support lever, the arm extending between the front body support post and support frame and being rotationally connected at one end to the post and rotationally connected at the other end to the support frame so that the seat and front body support are maintained at a constant angle with respect to a flat ground surface as the position stabilizing arm and support lever move rotationally about the support frame and post, the vertical gait measurement sensor rotationally connected to the forward gait measurement sensor;

an adjustable body weight support spring means rotationally connected on the support frame for applying a full or partial weight-bearing supporting force to the support lever so that the seat, front body support and user are able to move up or down responsive to the variable force supplied by the user as the user walks, stands or sits;

a control lever mounted on the adjustable body weight support spring means so that upon movement of the control lever an off center circular disk is turned which releases a gas control pin to limit the movement of a pressurized gas within the adjustable body weight support spring means so that the movement of the seat and front body support can be locked at variable fixed elevations including a sitting height position to allow a user to enter or exit the walker from a sitting position and hold the seat, front body support and user in a continuous sitting position without the application of the user's body weight force or force by another person and so that upon further movement of the control lever the off center circular disk is turned to activate the gas control pin to release the movement of the pressurized gas within the adjustable body weight support spring means so that the seat, front body support and user are released from a sitting position or fixed elevation to a standing or walking position supported by the adjustable full or partial body weight support spring means.

16. The gait analysis system of claim 14 wherein the lateral gait measurement sensor comprises a lateral rotary encoder, the lateral rotary encoder having a lateral rotary encoder output shaft, the lateral rotary encoder output shaft connected to a wheel-driven axle of a lateral omniwheel making contact with the fixed surface, the lateral omniwheel rotating in a lateral direction with user ambulation on the body support system over the fixed surface whereby a lateral rotary encoder output signal comprises the lateral gait measurement sensor output signal and provides a real time lateral user movement data.

17. The gait analysis system of claim 14 wherein the lateral gait measurement sensor comprises a lateral rotary encoder, the lateral rotary encoder having a lateral rotary encoder output shaft, the lateral rotary encoder mounted on the body support system, the lateral rotary encoder output shaft connected to a lateral rotational element of the body support system that rotates in a lateral direction with user ambulation on the body support system over the fixed surface whereby a lateral rotary encoder output signal comprises the lateral gait measurement sensor output signal and provides a real time lateral user movement data proportional to the rotation of the lateral rotational element.

18. The gait analysis system of claim 11 further comprising a heel strike bi-state sensor and a toe off bi-state sensor for each foot of the user, the heel strike bi-state sensor activated by the user to a first heel bi-state signal output during a heel strike time period of the heel strike of the fixed surface to a heel off of the fixed surface and a second heel bi-state signal output during a heel off time period when the heel is not in contact with the fixed surface during a gait cycle; the toe off bi-state sensor activated by the user to a first toe bi-state signal output during a toe off time period when the toe leaves the fixed surface to when the toe makes contact with the fixed surface during the gait cycle and a second toe bi-state signal output during a toe contact period when the toe is in contact with the fixed surface, the first and second heel bi-state signal output signals and the first and second toe bi-state signal outputs signals each comprising one of the plurality of gait sensor signals.

19. The gait analysis system of claim 18 further comprising a gait parameter video analysis processor for processing the user video sensor output signal, the gait parameter video analysis processor having one or more processed gait parameter outputs provided to the gait analysis personnel.

20. The gait analysis system of claim 11 further comprising:
a foot pressure level sensor having an array of foot variable pressure level sensors having variable pressure level outputs comprising one the plurality of gait sensor signals for processing by the gait analysis processor to a foot variable pressure level data displayed to the gait analysis personnel as a foot variable pressure video image of the user; and
the one or more processed gait parameter outputs comprising a gait parameter video image of the user.

21. The gait analysis system of claim 20 wherein the plurality of gait sensor signals for processing by the gait analysis processor comprises one or more electromyography gait sensor signals provided from one or more user-attached electromyography sensors for processing by the gait analysis processor to an electromyography signal data displayed to the gait analysis personnel as an electromyography graphical data display.

* * * * *